(12) United States Patent
Chiou et al.

(10) Patent No.: US 10,232,368 B2
(45) Date of Patent: *Mar. 19, 2019

(54) HIGH-SPEED ON DEMAND DROPLET GENERATION AND SINGLE CELL ENCAPSULATION DRIVEN BY INDUCED CAVITATION

(71) Applicant: The Regents of the University of California, Oakland, CA (US)

(72) Inventors: Pei-Yu E. Chiou, Los Angeles, CA (US); Ting-Hsiang S. Wu, Culver City, CA (US); Sung-Yong Park, Kent Vale (SG); Michael A. Teitell, Tarzana, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/930,054

(22) Filed: Nov. 2, 2015

(65) Prior Publication Data

US 2016/0158752 A1 Jun. 9, 2016

Related U.S. Application Data

(63) Continuation of application No. 13/370,196, filed on Feb. 9, 2012, now Pat. No. 9,176,504.

(60) Provisional application No. 61/442,009, filed on Feb. 11, 2011.

(51) Int. Cl.
*B01L 3/00* (2006.01)
*G05D 11/13* (2006.01)
(Continued)

(52) U.S. Cl.
CPC ......... *B01L 3/502715* (2013.01); *B01J 13/04* (2013.01); *B01L 3/502761* (2013.01);
(Continued)

(58) Field of Classification Search
CPC .......... B01L 2200/0673; B01L 3/0289; B01L 2400/02; B01L 2400/0442; B01L 2400/054; G01N 29/2418; G01N 2291/02433

See application file for complete search history.

(56) References Cited

U.S. PATENT DOCUMENTS 6,143,496 A 11/2000 Brown et al.
7,582,482 B2 9/2009 Dasgupta et al.
(Continued)

FOREIGN PATENT DOCUMENTS

CN 1521500 A 8/2004
JP H05-240872 A 9/1993
(Continued)

OTHER PUBLICATIONS

U.S. Office Action dated Oct. 10, 2012 issued in U.S. Appl. No. 12/852,320.
(Continued)

*Primary Examiner* — Brian R Gordon
(74) *Attorney, Agent, or Firm* — Tom Hunter; Weaver Austin Villeneuve & Sampson LLP

(57) ABSTRACT

Methods and devices for the formation of droplets of a first fluid in a second fluid and the encapsulation of particles or cells within such droplets are disclosed. Impetus for droplet formation is provided by the creation of a transient bubble, which may be induced using a pulsed laser. Droplet volume and the frequency at which droplets are formed can be controlled by modulation of the pulsed laser. The disclosed methods and devices are particularly suitable for use in microfluidic devices.

16 Claims, 13 Drawing Sheets

(51) Int. Cl.
  *B01J 13/04* (2006.01)
  *G01N 29/24* (2006.01)
  *G01N 15/10* (2006.01)
  *G01N 21/64* (2006.01)
  *G01N 15/14* (2006.01)

(52) U.S. Cl.
  CPC .... *B01L 3/502784* (2013.01); *G01N 29/2418* (2013.01); *G05D 11/13* (2013.01); *B01L 2200/0636* (2013.01); *B01L 2200/0647* (2013.01); *B01L 2200/0668* (2013.01); *B01L 2200/0673* (2013.01); *B01L 2300/0816* (2013.01); *B01L 2400/0403* (2013.01); *B01L 2400/0442* (2013.01); *G01N 15/10* (2013.01); *G01N 21/64* (2013.01); *G01N 2015/1481* (2013.01); *G01N 2291/02433* (2013.01); *Y10T 137/0318* (2015.04); *Y10T 137/2496* (2015.04)

(56) References Cited

U.S. PATENT DOCUMENTS

| | | | |
|---|---|---|---|
| 8,062,903 | B2 | 11/2011 | Chiu et al. |
| 8,127,624 | B2 | 3/2012 | Hashimoto et al. |
| 8,136,553 | B2 | 3/2012 | Baroud et al. |
| 8,206,994 | B2 | 6/2012 | Baroud et al. |
| 8,268,633 | B2 | 9/2012 | Ramsey et al. |
| 8,383,061 | B2 | 2/2013 | Prakash et al. |
| 8,506,905 | B2 | 8/2013 | Takeuchi et al. |
| 8,506,907 | B2 | 8/2013 | Angelescu |
| 8,563,325 | B1 | 10/2013 | Bartsch et al. |
| 8,592,215 | B2 | 11/2013 | Quake et al. |
| 9,176,504 | B2 | 11/2015 | Chiou et al. |
| 9,364,831 | B2 | 6/2016 | Chiou et al. |
| 10,071,359 | B2 | 9/2018 | Kung et al. |
| 2002/0005354 | A1 | 1/2002 | Spence et al. |
| 2002/0029814 | A1 | 3/2002 | Unger et al. |
| 2002/0037499 | A1 | 3/2002 | Quake et al. |
| 2003/0198523 | A1 | 10/2003 | Bohm et al. |
| 2006/0128006 | A1 | 6/2006 | Gerhardt et al. |
| 2006/0177348 | A1 | 8/2006 | Yasuda et al. |
| 2006/0246575 | A1 | 11/2006 | Lancaster et al. |
| 2008/0032295 | A1 | 2/2008 | Toumazou et al. |
| 2008/0196778 | A1 | 8/2008 | Baroud et al. |
| 2009/0090422 | A1 | 4/2009 | Baroud et al. |
| 2011/0030808 | A1 | 2/2011 | Chiou et al. |
| 2011/0059556 | A1 | 3/2011 | Strey et al. |
| 2011/0114190 | A1 | 5/2011 | Wen et al. |
| 2011/0177586 | A1 | 7/2011 | Ismagilov et al. |
| 2012/0236299 | A1 | 9/2012 | Chiou et al. |
| 2013/0183210 | A1 | 7/2013 | Wiyatno et al. |
| 2014/0212986 | A1 | 7/2014 | Angelescu et al. |
| 2016/0296933 | A1 | 10/2016 | Chiou et al. |

FOREIGN PATENT DOCUMENTS

| | | |
|---|---|---|
| JP | 2001-158099 A | 6/2001 |
| JP | 2003-514236 A | 4/2003 |
| JP | 2004-65110 A | 3/2004 |
| JP | 2007-515936 A | 6/2007 |
| JP | 2009-100698 A | 5/2009 |
| WO | WO 01/35071 A2 | 5/2001 |
| WO | WO 2005/023391 A2 | 3/2005 |
| WO | WO 2010/092845 A1 | 8/2010 |
| WO | WO 2012/009320 A2 | 1/2012 |
| WO | WO 2013/120016 A2 | 8/2013 |

OTHER PUBLICATIONS

U.S. Final Office Action dated Aug. 1, 2013 issued in U.S. Appl. No. 12/852,320.
U.S. Office Action dated Mar. 12, 2014 issued in U.S. Appl. No. 12/852,320.
U.S. Final Office Action dated Jan. 2, 2015 issued in U.S. Appl. No. 12/852,320.
U.S. Office Action dated Jul. 16, 2015 issued in U.S. Appl. No. 12/852,320.
U.S. Notice of Allowance dated Feb. 10, 2016 issued in U.S. Appl. No. 12/852,320.
U.S. Office Action dated Jan. 2, 2014 issued in U.S. Appl. No. 13/370,196.
U.S. Final Office Action dated Aug. 20, 2014 issued in U.S. Appl. No. 13/370,196.
U.S. Advisory Action dated Mar. 5, 2015 issued in U.S. Appl. No. 13/370,196.
U.S. Notice of Allowance dated Jun. 5, 2015 issued in U.S. Appl. No. 13/370,196.
U.S. Notice of Allowance dated Jun. 24, 2015 issued in U.S. Appl. No. 13/370,196.
PCT International Search Report and Written Opinion dated Dec. 20, 2013 issued in PCT/US2013/025434.
PCT International Preliminary Report on Patentability and Written Opinion dated Aug. 12, 2014 issued in PCT/US2013/025434.
Australian Patent Examination Report No. 1 dated Sep. 15, 2015 issued in AU 2013216804.
Australian Patent Examination Report No. 2 dated Jun. 6, 2016 issued in AU 2013216804.
Chinese Office Action (brief description in English) dated Jul. 24, 2015 issued in CN 201380016299.3.
Chinese Second Office Action (brief description in English) dated Mar. 16, 2016 issued in CN 201380016299.3.
European Extended Search Report dated Jan. 7, 2016 issued in EP 13 74 6888.
Reply Letter to European Extended Search Report dated Aug. 3, 2016 in EP 13 74 6888.
Japanese Office Action dated Oct. 7, 2016 issued in JP 2014-556753.
Applegate, Jr. et al., (2006) "Microfluidic sorting system based on optical waveguide integration and diode laser bar trapping," *Lab on a Chip,* 6:422-426 [Downloaded by University of California—Los Angeles on Apr. 18, 2013 19:29:53. Published on Jan. 20, 2006 on http://pubs.rsc.org | doi:10.1039/B512576F].
Baret et al., (2009) "Fluorescence-activated droplet sorting (FADS): efficient microfluidic cell sorting based on enzymatic activity," *Lab on a Chip,* 9:1850-1858 [Downloaded by University of California—Los Angeles on Apr. 18, 2013 19:18:09. Published on Apr. 23, 2009 on http://pubs.rsc.org | doi:10.1039/B902504A].
Chiou et al., (Jul. 21, 2005) "Massively parallel manipulation of single cells and microparticles using optical images," *Nature,* 436:370-372 [doi :10.1038/nature03831].
Cho et al., (2010) "Human mammalian cell sorting using a highly integrated micro-fabricated fluorescence-activated cell sorter (μFACS)," *Lab on a Chip,* 10:1567-1573 [Downloaded by University of California—Los Angeles on Apr. 18, 2013 19:31:47. Published on Apr. 9, 2010 on http://pubs.rsc.org | doi:10.1039/C000136H].
Di Carlo et al., (Nov. 27, 2007) "Continuous inertial focusing, ordering, and separation of particles in microchannels," *PNAS of the United States of America,* 104(48):18892-18897.
El-Sayed et al., (2006) "Selective laser photo-thermal therapy of epithelial carcinoma using anti-EGFR antibody conjugated gold nanoparticles," *Cancer Letters,* 239:129-135.
Fu et al., (Nov. 1999) "A microfabricated fluorescence-activated cell sorter," *Nature Biotechnology,* 17:1109-1111 [© 1999 Nature America Inc. http://biotech.nature.com].
Fu et al., (Jun. 1, 2002) "An integrated microfabricated cell sorter," *Analytical Chemistry,* 74(11):2451-2457.
Godin et al., (2008) "Microfluidics and photonics for Bio-System-on-a-Chip: A review of advancements in technology towards a microfluidic flow cytometry chip," *J. Biophoton.,* 1(5):355-376. [DOI 10.1002/jbio.200810018].
He et al., (2005) "Selective Encapsulation of Single Cells and Subcellular Organelles into Picoliter- and Femtoliter-Volume Droplets," *Analytical Chemistry,* 77(6):1539-1544.
Hellman et al., (Jun. 15, 2007) "Laser-Induced Mixing in Microfluidic Channels," *Analytical Chemistry,* 79(12):4484-4492.

(56) References Cited

OTHER PUBLICATIONS

Hessel et al., (2004) *Chemical Micro Process Engineering:Modelling and Reactions*, New York: Wiley-VCH Verlag GmbH & Co. KGaA, Weinheim, 36 pages.
Ho et al., (2005) "Micromachined electrochemical T-switches for cell sorting applications," *Lab on a Chip*, 5:1248-1258 [Downloaded by University of California—Los Angeles on Apr. 18, 2013 19:05:23. Published on Sep. 21, 2005 on http://pubs.rsc.org | doi:10.1039/B507575K].
Holmes et al., (2007) "Bead-based immunoassays using a microchip flow cytometer," *Lab on a Chip*, 7:1048-1056 [Downloaded by University of California—Los Angeles on Apr. 18, 2013 19:09:02. Published on Jun. 14. 2007 on http://pubs.rsc.org | doi:10.1039/B707507N].
Hsiung et al., (2006) "Micro-droplet formation utilizing microfluidic flow focusing and controllable moving-wall chopping techniques," *J. Micromechanics and Microengineering*, 16:2403-2410 [Downloaded on Apr. 18, 2013 at 19:11, http://iopscience.iop.org/0960-1317/16/11/022].
Huang et al., (2006) "Cancer Cell Imaging and Photothermal Therapy in the Near-Infrared Region by Using Gold Nanorods," *J. Am. Chemical Society*, 128:2115-2120.
Huh et al., (2003) "Reversible Switching of High-Speed Air-Liquid Two-Phase Flows Using Electrowetting-Assisted Flow-Pattern Change," *JACS*, 125:14678-14679.
Hur et al., (2010) "Sheathless inertial cell ordering for extreme throughput flow cytometry," *Lab on a Chip*, 10:274-280 [Downloaded by University of California—Los Angeles on Apr. 18, 2013 19:12:27. Published on Dec. 18, 2009 on http://pubs.rsc.org | doi:10.1039/B919495A].
Ibrahim et al., (2003) "High-speed cell sorting: fundamentals and recent advances," *Current Opinion in Biotechnology*, 14(1):5-12.
Idota et al., (2005) "Microfluidic Valves Comprising Nanolayered Thermoresponsive Polymer-Grafted Capillaries," *Advanced Materials*, 17:2723-2727.
Irimia, Daniel and Toner, Mehmet (Mar. 2006) "Cell handling using microstructured membranes," *Lab on a Chip*, 6:345-352 [Downloaded by University of California—Los Angeles on Apr. 18, 2013 19:10:43. Published on Feb. 8, 2006 on http://pubs.rsc.org | doi:10.1039/B515983K].
Jensen, K. (Jun. 25, 1998) "Chemical kinetics—Smaller, faster chemistry," *Nature*, 393:735-737.
Jensen, K.F. (Jan. 2001) "Microreaction engineering—is small better?" *Chemical Engineering Science*, 56:293-303.
Kim et al., (Jul. 2007) "Novel platform for minimizing cell loss on separation process: Droplet-based magnetically activated cell separator," *Review of Scientific Instruments*, 78:074301-1-7.
Leary, James F., (2005) "Ultra high-speed sorting," *International Society for Analytical Cytology, Cytometry Part A* 67A:76-85.
Li et al., (2010) "Two Same-Sized Droplets Coalescence by Laser-Induced Cavitation Bubbles," *14th International Conference on Miniaturized Systems for Chemistry and Life Sciences*, Oct. 3-7, 2010, Groningen, The Netherlands, pp. 1088-1090.
Li et al., (2011) "Fast on-demand droplet fusion using transient cavitation bubbles," *Lap on a Chip*, 11:1879-1885 [Published on Apr. 12, 2011. Downloaded by Korea Advanced Institute of Science & Technology / KAIST on Jan. 11, 2013 00:55:20.].
Marcus et al., (May 1, 2006) "Microfluidic single-cell mRNA isolation and analysis," *Analytical Chemistry*, 78(9): 3084-3089.
Mehta et al., (Jan. 5-8, 2009) "Magnetic Nanowire-Enhanced Optomagnetic Tweezers," *Proceeding of the 2009 4th IEEE International Conference on Nano/Micro Engineered and Molecular Systems*, Shenzhen, China, pp. 1004-1007.
Melin et al., (2007) "Microfluidic Large-Scale Integration: The Evolution of Design Rules for Biological Automation," *Annual Review of Biophysics and Biomolecular Structure*, 36:213-231 [Annu. Rev. Biophys. Biomol. Struct. 2007.36:213-231. Downloaded from www.annualreviews.org by University of California—Los Angeles—Law Library UCLA on Apr. 18, 2013. For personal use only].
Panaro et al., (Feb. 2005) "Micropillar array chip for integrated white blood cell isolation and PCR," *Biomolecular Engineering*, 21:157-162.
Park et al., (Jan. 2010) "A pulse laser-driven microfluidic device for ultrafast droplet generation on demand and single-cells encapsulation," *14th International Conference on Miniaturized Systems for Chemistry and Life Sciences*, Groningen, The Netherlands, pp. 2129-2131.
Park et al., (2011) "High-speed droplet generation on demand driven by pulse laser-induced cavitation," *Lab on a Chip*, 11(6):1010-1012, 3 pages.
Park et al., (2011) "High-speed droplet generation on demand driven by pulse laser-induced cavitation," *Lab on a Chip*, 11(6):1010-1012, 9 pages [NIH Public Access, NIH-PA Author Manuscript].
Pitsillides et al., (Jun. 2003) "Selective cell targeting with light-absorbing microparticles and nanoparticles," *Biophys J*, 84(6):4023-4032.
Shirasaki et al., (Feb. 1, 2006) "On-Chip Cell Sorting System Using Laser-Induced Heating of a Thermoreversible Gelation Polymer to Control flow," *Analytical Chemistry*, 78(3):695-701.
Sun et al., (2007) "Design, simulation and experiment of electroosmotic microfluidic chip for cell sorting," *Sens. Actuators A.* 133(2):340-348.
Tandiono et al., (2010) "Creation of cavitation activity in a microfluidic device through acoustically driven capillary waves," *Lab Chip*, 10:1848-1855.
Vogel et al., (Dec. 2005) "Mechanisms of femtosecond laser nanosurgery of cells and tissues," *Applied Physics B—Lasers and Optics*, 81:1015-1047.
Wang et al., (2007) "High-density microfluidic arrays for cell cytotoxicity analysis," *Lab on a Chip*, 7:740-745 [Downloaded by University of California—Los Angeles on Apr. 18, 2013 19:50:05. Published on Apr. 4, 2007 on http://pubs.rsc.org | doi:10.1039/B618734J].
Wang et al., (Jan. 2005) "Microfluidic sorting of mammalian cells by optical force switching," *Nature Biotechnology*, 23(1):83-87.
Wu et al., (Jan. 18, 2010) "Image patterned molecular delivery into live cells using gold particle coated substrates," *Optics Express*, 18(2):938-946.
Wu et al., (2012) "Pulsed laser triggered high speed microfluidic fluorescence activated cell sorter," *Lab on a Chip*, 12:1378-1383 [Downloaded by University of California—Los Angeles on Apr. 18, 2013 19:33:06. Published on Feb. 15, 2012 on http://pubs.rsc.org | doi:10.1039/C2LC21084C].
Wu et al., (Oct. 6, 2008) "Pulsed laser triggered high speed microfluidic switch," *Appl. Phys. Lett.* 93, 144102-1-3. [Downloaded Oct. 10, 2008 to 131.252.222.209. Redistribution subject to AIP license or copyright; see http://apl.aip.org/apl/copyright.jsp].
Xu, Jie and Attinger, Daniel, (2008) "Drop on demand in a microfluidic chip," *J. Micromechanics and Microengineering*, 18:065020, 11 pp [downloaded on Apr. 18, 2013 at 19:43, http://iopscience.iop.org/0960-1317/18/6/065020].
Yao et al., (Nov./Dec. 2005) "Elevation of plasma membrane permeability by laser irradiation of selectively bound nanoparticles," *J Biomed Opt*, 10(6):064012-1-064012-8.
Yoshida et al., (Mar. 2005) "Enhancement of Chemical Selectivity by Microreactors," *Chemical Engineering & Technology*, 28(3):259-266.
Zeng et al., (2009) "Microvalve-actuated precise control of individual droplets in microfluidic devices," *Lab on a Chip*, 9:1340-1343 [Downloaded by University of California—Los Angeles on Apr. 18, 2013 19:50:54. Published on Mar. 27, 2009 on http://pubs.rsc.org | doi:10.1039/B821803J].
Zhong et al., (2008) "A microfluidic processor for gene expression profiling of single human embryonic stem cells," *Lab on a Chip*, 8:68-74 [Downloaded on Apr. 18, 2013 19:20:57. Published on Nov. 2, 2007 on http://pubs.rsc.org | doi:10.1039/B712116D].
Zhong et al., (2008) "Microfluidic Devices for Investigating Stem Cell Gene Regulation via Single-Cell Analysis," *Current Medicinal Chemistry*, 15(28):2897-2900.
Zwaan et al., (2007) "Controlled cavitation in microfluidics," *Phys. Rev. Lett.*, 98:2545, 4 pages.

(56) References Cited

OTHER PUBLICATIONS

U.S. Office Action dated Feb. 16, 2017 issued in U.S. Appl. No. 15/094,919.
U.S. Final Office Action dated Nov. 3, 2017 issued in U.S. Appl. No. 15/094,919.
Australian Patent Examination Report No. 1 dated Nov. 27, 2017 issued in AU 2016234996.
Japanese Decision of Rejection dated May 8, 2017 issued in JP 2014-556753.

HIGH-SPEED ON DEMAND DROPLET GENERATION AND SINGLE CELL ENCAPSULATION DRIVEN BY INDUCED CAVITATION

CROSS-REFERENCE TO RELATED APPLICATIONS

This application is a continuation of U.S. patent application Ser. No. 13/370,196, filed on Feb. 9, 2012, issued as U.S. Pat. No. 9,176,504 which claims benefit of and priority to USSN 61/442,009, filed on Feb. 11, 2011, both of which are incorporated herein by reference in their entirety for all purposes.

STATEMENT OF GOVERNMENTAL SUPPORT

This invention was made with government support under Grant Number EY018228, awarded by the National Institutes of Health, and Grant Numbers 0747950, 0852701, and 0901154, awarded by the National Science Foundation. The government has certain rights in the invention.

The invention described herein was made in the performance of work under NASA cooperative agreement NCC2-1364, and is subject to the provisions of Public Law 96 -517 (35 USC 202 ) in which the Contractor has elected to retain title.

FIELD

The present invention relates to the field of microfluidics. In certain embodiments methods and devices are provided for the high speed formation of droplets and/or the encapsulation of droplets, particles, and/or cells.

BACKGROUND

Microfluidic devices have attracted great interest as they to provide a platform for performing analyses on extremely small volumes of fluid, and when produced utilizing photolithography techniques can be manufactured inexpensively. These devices have the potential to act as a "lab on a chip", integrating multiple functionalities including, for example, sample preparation, thermal cycling to support the polymerase chain reaction, and absorbance or fluorescence monitoring. Their compact size makes them particularly suitable for use in portable devices, potentially allowing the performance of sophisticated analyses in a clinician's office or in the field. One of the challenges with using microfluidic devices in the analysis of multiple samples, however, is sample compartmentalization. While a conventional laboratory analyzer may utilize a series of cuvettes or similar receptacles to prevent contamination between samples this approach is difficult to implement with small volumes of fluid, where interactions with device surfaces can supersede bulk flow properties.

Typical microfluidic devices utilize a single fluid phase that flows continuously through the device. Introduction of a discrete volume of fluid test sample or reagent into such a device leads to the formation of a fluid segment that moves through the channels of the apparatus. Unfortunately, such a fluid segment will tend to become dispersed due to forces such as diffusion and turbulence within the flow channel. In addition it is possible for components of the fluid segment to interact with the walls of channels of the microfluidic device, only to be released at a later time. Such phenomena can result in contamination between fluid segments and results in the need to design such microfluidic chips with features to reduce turbulence within fluid channels and to design test protocols that incorporate time consuming washing or flushing of the interior volume between samples. In addition, dispersion of fluid segments makes it difficult to provide reproducible volumes and concentrations of fluid segment contents for characterization reactions.

One approach to resolving this issue has been the introduction of digital microfluidic devices, in which sample fluids for analysis or other treatment are introduced into the channels of the device in the form of discrete, low volume droplets. For example, introducing aqueous samples with biochemical or biological contents as aqueous droplets that travel within a channel containing an immiscible oil medium reduces interaction with the channel wall and prevents dispersion, minimizing contamination between droplets. Reagents used in the characterization of such samples can be treated similarly. In order to be effective, however, a digital microfluidic device requires a mechanism for high-speed droplet generation with precise volume control in order to fully realize accurate, high throughput analysis.

Passive mechanisms may be used for rapid, continuous droplet generation as a function of flow through such a device. Highly uniform droplets can be generated at a rate of thousands of drops per second in this fashion (Yobas et al. (2006) *Lab on a Chip,* 6:1073-1079). U.S. Pat. No. 7,759, 111 describes such a device, where droplets are sheared from a stream of aqueous media by a flow of immiscible oil. Another example of a passive device is disclosed in WO 2010/110843A1, in which a barrier intruding into a fluid channel acts in combination with fluid and flow characteristics of the channel to form vortices that provide periodic variations in pressure that drive droplet formation. Such devices, however, do not provide on demand generation of a droplet containing specifically designated volume of sample fluid (for example, a volume containing a particular cell of interest) and do not lend themselves to the production of individual droplets with different volumes. This limits their utility for the characterization of different samples volumes and in the performance of a variety of testing protocols.

Active methods for droplet generation, which rely on the use of an applied force to drive droplet formation, can address these issues. Such devices may incorporate physical components that regulate flow through the device. One example of this is the use of pneumatically driven microvalves that are integrated into the microfluidic device (Zeng et al. (2009) *Lab on a Chip* 9:134-1343), which permitted controlled droplet formation at rates as high as 100 droplets per second. Another example of this approach is the use of a movable wall of flexible material (PDMS) that is integrated into the microfluidic chip and driven by air pressure to periodically interrupt the flow of a fluid phase in order to provide a dispersion (Hsiung et al. (2006) *J. Micromechanics and Microengineering,* 16: 2403-2410), which demonstrated rates of droplet formation as high as 20 per second. Yet another example, US 2010/0059120, discloses the use of a two channels connected by an opening, in which a flow interruptor in one channel can be triggered to block fluid flow and force a portion of its contents into the second channel. Another example of such a device is described in US 2010/0163412, which discloses a device that incorporates a flexible fluid reservoir that is compressed briefly by an imbedded piezoelectric device to generate pressure for droplet formation. Such features add significantly complexity to the design of these microfluidic devices, further complicating the manufacturing process. The mechanical nature of such approaches limits the frequency at which droplets can be produced and may show changes in performance over time. In addition, these approaches tend to produces droplet populations with greater variation in droplet size than those produced using passive devices.

Other approaches to active droplet generation have relied on the use of massless or essentially massless energies applied to the device in order to avoid the disadvantages of mechanical components. Some of these utilize the application of electrical fields to the device to alter fluid flow or change the properties of the interface between two fluids in order to facilitate droplet formation. This can require large differences in conductivity between the fluids involved, which limits the utility of such devices. For example, US 2006/0231398 discloses the use of potential differences to move droplets between immiscible low and high resistance fluids by electrowetting, utilizing a potential difference to temporarily lower the surface tension at the interface between the fluids until the existing flow pattern is sufficient to generate droplets. A similar approach is described in WO 2010/151776, in which a potential difference drives a combination of effects, including electrokinetic flow and interference in the interface between two immiscible fluids, to generate droplets. Yet another example of the use of potential differences to drive droplet formation is found in WO 2011/023405A1, which discloses a combination of a nozzle structure and establishment of a potential difference to electrospray droplets of a conductive fluid into a fluid dielectric. An approach that does not require large conductivity differences between the fluids involved in droplet formation is disclosed in US 2005/0031657, which describes heating a portion of a container within the device using a resistance heater until a portion of the fluid stored therein is vaporized. Pressure from the vaporized fluid pushes a portion of remaining fluid through a nozzle into an immiscible fluid. Droplet generation from this approach is relatively slow, however, producing only around 15-25 droplets per second per nozzle. While these approaches avoid the use of mechanical components, they require the incorporation of electrodes, resistance heaters, or similar components into the device. This adds complexity to the design of the device and further requires the use of supporting features for reliably supplying current.

SUMMARY

In various embodiments novel methods and devices for rapidly and reproducibly generating droplets of a first fluid in a second fluid are described herein. The fluids may be immiscible, where the immiscible fluids can include fluids that are not significantly soluble in one another, fluids that do not mix for a period of time due to physical properties such as density or viscosity, and fluids that do not mix for periods of time due to laminar flow. Droplet formation is driven by the expansion and subsequent contraction of transient bubbles (such as cavitation bubbles) within the first fluid. Alternatively, the bubble formation within a first fluid may cause it to act on a second fluid thereby driving generation of droplets of the second fluid in a third fluid. Cavitation bubbles can be generated using a directed energy source, thereby removing the need to incorporate electrodes, heaters, or similar components into devices incorporating the invention. Suitable directed energy sources include, but are not limited to, a pulse laser, use of which permits on demand formation of highly reproducible droplets at speeds from less than 1 up to 100,000 droplets per second. Droplet volume can be controlled, with droplet volumes, in certain embodiments ranging from about 1 to about 150 picoliters. In certain embodiments live cells can be captured within such droplets, with high cell viability, in certain embodiments of up to 92.07%. Since mechanical valves or pumps are not needed these methods and devices are particularly suitable for use in microfluidic devices.

In one embodiment a first fluid and a second fluid, which may be immiscible, are operatively coupled. In certain embodiments the operative coupling can take the form of a fluid communication. In other embodiments a flexible membrane may be interposed between the first fluid and the second fluid. Generation of a cavitation bubble within the first fluid generates sufficient velocity and/or impulse and/or displacement to the first fluid to move a controlled volume of the second fluid. In certain embodiments such a cavitation bubble expands and contracts within 1 millisecond, can move a controlled volume of about 1 microliter or less. Such cavitation bubbles may be produced by irradiation, for example by a pulse laser. In some embodiments the volume of the controlled volume of the second fluid can be controlled by the energy and/or pulse frequency, and/or wavelength of the pulse laser, which in turn may be modulated by a controller.

In another embodiment a first fluid path and a second fluid path are coupled via an opening. In some embodiments fluids in the first and second fluid paths are immiscible. Generation of a cavitation bubble within the first fluid path imparts sufficient velocity to a portion of the first fluid to cause a droplet of the first fluid to move across the opening and into the second fluid path. In certain embodiments the opening may be configured as a port, a channel, or nozzle. Such cavitation bubbles may be produced by irradiation, for example by a pulse laser. In some embodiments intensity, duration, and/or position of the laser irradiation can be modulated the volume of the droplet.

In another embodiment of the invention a first fluid path and a second fluid path are in fluid communication, and the second fluid path is coupled to a third fluid path via an opening. In some embodiments fluids in the second and third fluid paths are immiscible. Generation of a cavitation bubble within the first fluid path imparts sufficient velocity to a portion of the second fluid to cause a droplet of the second fluid to move through the opening and into the third fluid path. In certain embodiments the opening may be configured as a port, a channel, or nozzle. In some embodiments the second fluid may include particles and/or cells. The second fluid path may be monitored, with data produced by such monitoring being transmitted to a controller. In some embodiments cavitation bubbles are produced by irradiation, which may be initiated by a controller. Irradiation can be in the form of a laser pulse, and in some embodiments the volume of the droplet may be modulated using the intensity, duration, and position of the laser pulse.

In another embodiment a flexible membrane is interposed between a first fluid path and a second fluid path, and the second fluid path is coupled to a third fluid path via an opening. In some embodiments fluids in the second and third fluid paths are immiscible. Generation of a cavitation bubble within the first fluid path results in the elastic deformation of a portion of the flexible membrane into the second fluid path. This elastic deformation imparts sufficient velocity to a portion of the second fluid to cause a droplet of the second fluid to move through the opening and into the third fluid path. The opening may be configured as a controller. In some embodiments the second fluid may include particles and/or cells. The second fluid path may be monitored, with data produced by such monitoring being transmitted to a controller. In some embodiments cavitation bubbles are produced by irradiation, which may be initiated by a controller. Irradiation can be in the form of a laser pulse, and in some embodiments the volume of the droplet may be modulated using the intensity, duration, and position of the laser pulse.

In another embodiment of the invention a first fluid path and a second fluid path are connected by an opening, where the opening is positioned such that formation of a bubble in the first fluid path can induce a force that causes a droplet of the first fluid to move through the opening and into the second fluid path. In certain embodiments the opening may be configured as a port, a channel, or nozzle. In some embodiments the opening is configured as a nozzle. A controller is coupled to an energy source (such as, for example, a pulse laser) that can direct energy into the first fluid path to cause the formation of one or more bubbles. In some embodiments the bubble can be a cavitation bubble. In still other embodiments the energy source is a pulse laser; the controller may be configured to adjust the volume of the droplet by modulating the intensity, duration, and/or position of a laser pulse produced by a pulse laser.

In still another embodiment a first fluid path and second fluid path are positioned such that a flexible membrane is interposed between them. The flexible membrane is in turn positioned such that formation of a bubble within the first fluid path results in the elastic deformation of a portion of the flexible membrane, which in turn induces a force on fluid contained in the second fluid path. The second fluid path and a third fluid path are connected by an opening, which is disposed such that when such a force is exerted on the fluid of the second fluid path a droplet of the fluid is extruded through the opening into the third fluid path. A controller is configured to direct energy that results in the temporary formation of a bubble in the first fluid path. This temporary bubble can be a cavitation bubble. In certain embodiments the opening may be configured as a port, a channel, or nozzle. In some embodiments the opening is configured as a nozzle. In various embodiments a monitor may be configured to monitor the second fluid path or the third fluid path, where the monitor transmits the data gathered to the controller. In certain embodiments the controller may be configured to control the transfer of a designated volume of the fluid in the second fluid path into the third fluid path, where the designated volume is determined using data from the monitor.

In some embodiments a fluid path may include particles or cells that are encapsulated by droplets of the surrounding fluid that are extruded into another fluid path. A monitor may be included in some embodiments to characterize such particles or cells which, when coupled with a controller, may permit controlled encapsulation of specific particles or cells within a specified droplet.

In various embodiments devices for the generation of droplets are provided. In certain embodiments the device comprises a first fluid stream (e.g., microfluid stream) comprising a first fluid adjacent to a second fluid stream (e.g., microfluid stream) comprising a second fluid where the second fluid is immiscible in the first fluid. In certain embodiments the device comprises a first microfluidic channel comprising, containing and/or directing the first fluid stream; and a second microfluidic channel comprising, containing and/or directing the second fluid stream where the first microfluidic channel is adjacent to, or in proximity to, the first microfluidic channel and is in fluid communication with the second channel (e.g., via a port or a channel). In certain embodiments the second fluid comprises an aqueous fluid. In certain embodiments the first fluid comprises an oil or an organic solvent. In certain embodiments the first fluid comprises a solvent selected from the group consisting of carbon tetrachloride, chloroform, cyclohexane, 1,2-dichloroethane, dichloromethane, diethyl ether, dimethyl formamide, ethyl acetate, heptane, hexane, methyl-tert-butyl ether, pentane, toluene, and 2,2,4-trimethylpentane. In certain embodiments the first fluid comprises an oil. In certain embodiments the device comprises a third fluid stream disposed between the first microfluid stream and the second microfluid stream. In certain embodiments the device comprises a third fluid stream disposed between the second fluid and the port or channel. In certain embodiments the device further comprises a third fluid stream disposed in the second microfluidic channel between the port and the second fluid. In certain embodiments the third fluid stream contains droplets, cells, or particles that are to be encapsulated. In certain embodiments the port or channel comprises a nozzle. In certain embodiments the first and/or second microfluidic channel is formed from a material selected from the group consisting of glass, metal, ceramic, mineral, plastic, and polymer. In certain embodiments the first and/or second microfluidic channel is formed from an elastomeric material (e.g., polydimethylsiloxane (PDMS), polyolefin plastomers (POPs), perfluoropolyethylene (a-PFPE), polyurethane, polyimides, and cross-linked NOVOLAC® (phenol formaldehyde polymer) resin, and the like).

In certain embodiments the device produces a substantially continuous volume tuning of droplet ranging from about 0.1 fL or about 1 fL, or about 10 fL or about 50 fL, or about 100 fL, or about 500 fL up to about 1 µL, or about 500 nL, or about 1 nL, or about 500 pL, or about 400 pL or about 300 pL or about 200 pL or about 150 pL. In certain embodiments the device produces a substantially continuous volume tuning of droplet ranging from about 0.1 fL to about 1 µL, or about 0.1 fL up to about 500 nL, or about 1 fL up to about 1 nL, or about 1 fL up to about 500 pL, or about 500 fL up to about 500 pL or about 1 pL up to about 150 pL. In certain embodiments the device can provide on-demand droplet generation at a speed of greater than about 1,000, more preferably greater than about 2,000 droplets/sec, more preferably greater than about 4,000 droplets/sec, more preferably greater than about 6,000 droplets/sec, or more preferably greater than about 8,000 droplets/sec. In certain embodiments the device can provide on-demand droplet generation at a speed ranging from zero droplets/sec, 1 droplets/sec, 2 droplets/sec, about 5 droplets/sec, about 10 droplets/sec, about 20 droplets/sec, about 50 droplets/sec, about 100 droplets/sec, about 500 droplets/sec, or about 1000 droplets/sec, up to about 1,500 droplets/sec, about 2,000 droplets/sec, about 4,000 droplets/sec, about 6,000 droplets/sec, about 8,000 droplets/sec, about 10,000 droplets/sec, about 20,000 droplets/sec, about 50,000 droplets/sec, or about 100,000 droplets/sec. In certain embodiments the device can provide on-demand droplet generation at a speed of greater than about 1,000, more preferably greater than about 10,000, more preferably greater than about 20,000 droplets/sec, more preferably greater than about 40,000, more preferably greater than about 50,000 droplets/sec, more preferably greater than about 80,000, or more preferably greater than about 100,000 droplets/sec. In certain embodiments the device is present in (or a component of) a system comprising an energy source capable of forming a bubble in a fluid stream or a microchannel. In certain embodiments the energy source comprises an optical energy source or microwave emitter. In certain embodiments the energy source comprises a laser (e.g., a pulse laser). In certain embodiments the device and/or system are configured to excite vapor bubbles in the second microfluidic stream. In certain embodiments the device and/or system are configured to excite vapor bubbles in the second microfluidic channel in proximity to the port or channel. In certain embodiments the device and/or system are configured to excite vapor bubbles in a third microfluidic channel or chamber that is not in fluid communication with the first or second microfluidic stream. In certain embodiments the vapor bubbles are excited in a liquid or gel medium. In certain embodiments the where vapor bubbles are excited in an oil or non-aqueous medium. In certain embodiments the vapor bubbles are excited in a medium that comprises light-absorbing nano/microparticles (e.g. dye molecules, metal nanoparticles, and the like). In certain embodiments the device is disposed on a substrate comprising a material selected from the group consisting of a polymer, a plastic, a glass, quartz, a dielectric material, a semiconductor, silicon, germanium, ceramic, and a metal or metal alloy. In certain embodiments the device is integrated with other microfluidic components (e.g., microfluidic components such as PDMS channels, wells, valves, and the like). In certain embodiments the device is a component of a lab-on-a-chip.

In various embodiments systems are provided for the generation of droplets and/or the encapsulation of particles or cells. In certain embodiments the systems a device as described above (or below), and an excitation source for forming gas bubbles in a fluid. In certain embodiments the excitation source is a laser, a microwave source, or an ultrasonic energy source. In certain embodiments the system further comprises components for detecting particles or cells in the system (e.g., an optical detection system, an electrical detection system, a magnetic detection system, an acoustic wave detection system, an electrochemical detection system, and the like). In certain embodiments the components comprise an optical detection system for detecting scattering, fluorescence, or s ramen spectroscopy signal.

In various embodiments methods for generating droplets are provided. In certain embodiments the methods involve providing a device as described above (and below herein); and utilizing an energy source to form bubbles in the second microfluidic stream or the second microfluidic channel or in a third microfluidic channel or chamber to inject droplets into the first microfluidic stream or channel. In certain embodiments the utilizing an energy source comprises utilizing a pulse laser to excite cavitation bubbles in the second microfluidic stream or channel or in the third microfluidic channel or chamber.

In various embodiments methods of moving a controlled amount of a fluid are provided. In certain embodiments such methods comprise: generating a cavitation bubble in a first fluid, where the cavitation bubble imparts a sufficient velocity to a portion of the first fluid to thereby move a controlled volume of a second fluid that is operatively coupled to the first fluid. In certain embodiments the controlled volume of the second fluid is about 10 µL or less, or about 5 µL or less, or about 1 µL or less, or about 500 nL or less, or about 100 nL or less, or about 1 nL or less, or about 500 pL or less, or about 200 pL or less. In certain embodiments the cavitation bubble has a duration about 100 ms or less, or about 50 ms or less, or about 1 ms or less, or about 0.5 ms or less, or about 1 ms or less or about 0.5 ms or less, or about 0.1 ms or less, or about 0.05 ms or less. In certain embodiments the controlled volume of the second fluid is 1 µL or less and the duration of the cavitation bubble is about 1 ms or less. In certain embodiments the first fluid and the second fluid are in fluid communication. In certain embodiments a flexible membrane is interposed between the first fluid and the second fluid. In certain embodiments the first and second fluids are immiscible. In certain embodiments the cavitation bubble is generated by irradiation of a volume of the first fluid with a pulsed laser. In certain embodiments the method further comprises controlling the controlled volume of the second fluid using a controller that adjusts at least one of energy and/or pulse frequency, and/or wavelength of the pulsed laser. In certain embodiments the method comprises generating a plurality of separate and additional cavitation bubbles at a frequency of at least about 1000 Hz, or at least about 5,000 Hz, or at least about 10,000 Hz. In certain embodiments the controlled volume of the second fluid is about 500 nanoliters or less. In certain embodiments the controlled volume of the second fluid is about 200 pL or less. In certain embodiments the method is repeated at a frequency of about 1 kHz or greater, or at a frequency of about 5 kHz or greater, or at a frequency of about 10 kHz or greater.

In various embodiments methods for generating droplets in a device are provided. In certain embodiments the methods comprise: providing a first fluid path comprising a first fluid; a second fluid path comprising a second fluid; and an opening fluidly coupling the first fluid path to the second fluid path; and generating a cavitation bubble in the first fluid path, where the cavitation bubble imparts sufficient velocity and/or impulse and/or displacement to a portion of the first fluid so as to extrude a droplet of the first fluid across the opening and into the second fluid path. In certain embodiments the first fluid and the second fluid are immiscible fluids. In certain embodiments the first fluid is an aqueous fluid and the second fluid is an organic solvent or an oil. In certain embodiments the second fluid is an aqueous fluid and the first fluid is an organic solvent or an oil. In certain embodiments the opening is configured as a nozzle. In certain embodiments the cavitation bubble is generated by irradiation of a volume of the first fluid with a pulsed laser. In certain embodiments the method involves selecting at least one of an intensity, duration, wavelength and position of the laser pulse to thereby produce a desired volume of the droplet.

In certain embodiments methods for generating droplets in a device are provided comprising: providing a first fluid path comprising a first fluid; a second fluid path comprising a second fluid, the second fluid path in fluid communication with the first fluid path; a third fluid path comprising a third fluid; and an opening fluidly coupling the second fluid path to the third fluid path; and generating a cavitation bubble in the first fluid path, where the cavitation bubble imparts sufficient velocity to a portion of the second fluid to extrude a droplet of the second fluid across the opening and into the third fluid path. In certain embodiments the second fluid and the third fluid are immiscible fluids. In certain embodiments the second fluid is an aqueous fluid and the third fluid is an organic solvent or an oil. In certain embodiments the second fluid is an aqueous fluid and the third fluid is an organic solvent or an oil. In certain embodiments the the method further comprises monitoring the second fluid path and transmitting data generated by such monitoring to a controller. In certain embodiments the second fluid further comprises a particle. In certain embodiments the second fluid further comprises a cell. In certain embodiments the opening is configured as a nozzle. In certain embodiments the cavitation bubble is generated by irradiation of a volume of the first fluid. In certain embodiments the irradiation is initiated by a controller. In certain embodiments the irradiation is a laser pulse. In certain embodiments the method further comprises selecting at least one of an intensity, duration, wavelength, and position of the laser pulse to thereby produce a desired volume of the droplet.

In certain embodiments methods for generating droplets in a device are provided comprising: providing a first fluid path comprising a first fluid, a second fluid path comprising a second fluid, a third fluid path comprising a third fluid, a flexible membrane interposed between the first fluid path and the second fluid path, and an opening between the second fluid path and the third fluid path; and generating a cavitation bubble in the first fluid path that elastically deforms a portion of the flexible membrane (e.g., a membrane fabricated form an elastomeric material (e.g. polydimethylsiloxane (PDMS), polyolefin plastomers (POPs), perfluoropolyethylene (a-PFPE), polyurethane, polyimides, and cross-linked NOVOLAC® (phenol formaldehyde polymer) resin, and the like)) into the second fluid path, where the elastic deformation of the portion of the flexible membrane imparts sufficient velocity and/or impulse, and/or displacement to a portion of the second fluid to extrude a droplet of the second fluid across the opening and into the third fluid path. In certain embodiments the second fluid and the third fluid are immiscible fluids. In certain embodiments the second fluid is an aqueous fluid and the third fluid is an organic solvent or an oil. In certain embodiments the second fluid is an aqueous fluid and the third fluid is an organic solvent or an oil. In certain embodiments the method further comprises monitoring the fluid in the second fluid path and transmitting data generated by such monitoring to a controller.

In various embodiments devices for generating droplets are provided. In certain embodiments the devices comprise a first fluid path; a second fluid path; an opening between the first fluid path and the second fluid path, the opening disposed such that formation of a bubble in a fluid in the first fluid path induces a force in the in an amount effective to thereby extrude a droplet of the fluid from the first fluid path through the opening into the second fluid path; and a controller coupled to an energy source that is and operatively configured to cause the energy source to direct an energy that induces temporary formation of one or more bubbles in the first fluid path. In certain embodiments the bubble is a cavitation bubble. In certain embodiments the opening is configured as a nozzle. In certain embodiments the energy source a pulsed laser. In certain embodiments the controller is configured to adjust volume of the droplet as a function of at least one of an intensity of the laser pulse, a duration of the laser pulse, a wavelength of the laser pulse, and a position of the laser pulse within the first fluid channel.

In various embodiments devices for generating droplets are provided. In certain embodiments the devices comprise a first fluid path; a second fluid path; a third fluid path; a flexible membrane interposed between the first fluid path and the second fluid path, the flexible membrane disposed such that formation of a bubble in a fluid in the first fluid path induces a force that elastically deforms a portion of the flexible membrane; an opening between the second fluid path and the third fluid path, the opening disposed such that elastic deformation of a portion of the flexible membrane induces a force on a second fluid to thereby extrude a droplet of the second fluid from the second fluid path through the opening into the third fluid path; and a controller operatively configured to direct an energy that induces temporary formation of the bubble in the fluid in the first fluid path. In certain embodiments the bubble is a cavitation bubble. In certain embodiments the device further comprises a monitor configured to monitor the second or third fluid path, and further configured to transfer data from the monitor to the controller. In certain embodiments the controller is further configured to control a designated volume of the second fluid into the third fluid path, the designated volume being determined at least in part by data from the monitor.

In certain embodiments of any of the foregoing methods and devices, droplets are generated with droplet volume variations of about 10% or less, preferably about 5% or less, more preferably about 3% or less, or about 2% or less, or about 1% or less at repetition rates ranging from about 1 kHz up to about 10 kHz.

BRIEF DESCRIPTION OF THE DRAWINGS

FIG. 1A shows plasma generation within a volume of fluid as a result of irradiation with a focused laser pulse, followed by generation of a shockwave and cavitation bubble expansion and subsequent collapse. FIG. 1B shows a graph of a typical time course for expansion and subsequent collapse of a cavitation bubble.

DETAILED DESCRIPTION

In various embodiments devices and methods are provided for on-demand high speed droplet generation of droplets of controlled volume that ha e particular application in the field of microfluidics. In various embodiments, the methods and devices can also be used to encapsulate cells and/or particles, and/or other fluid droplets.

In various embodiments the devices and methods described herein utilize a novel controllable actuation mechanism, utilizing directed energy that induces short-lived cavitation bubbles. In some embodiments this energy is in the form of a pulse laser that provides bursts of optical energy, the intensity, duration, wavelength, and/or position of which can be controlled.

Figure 1A:
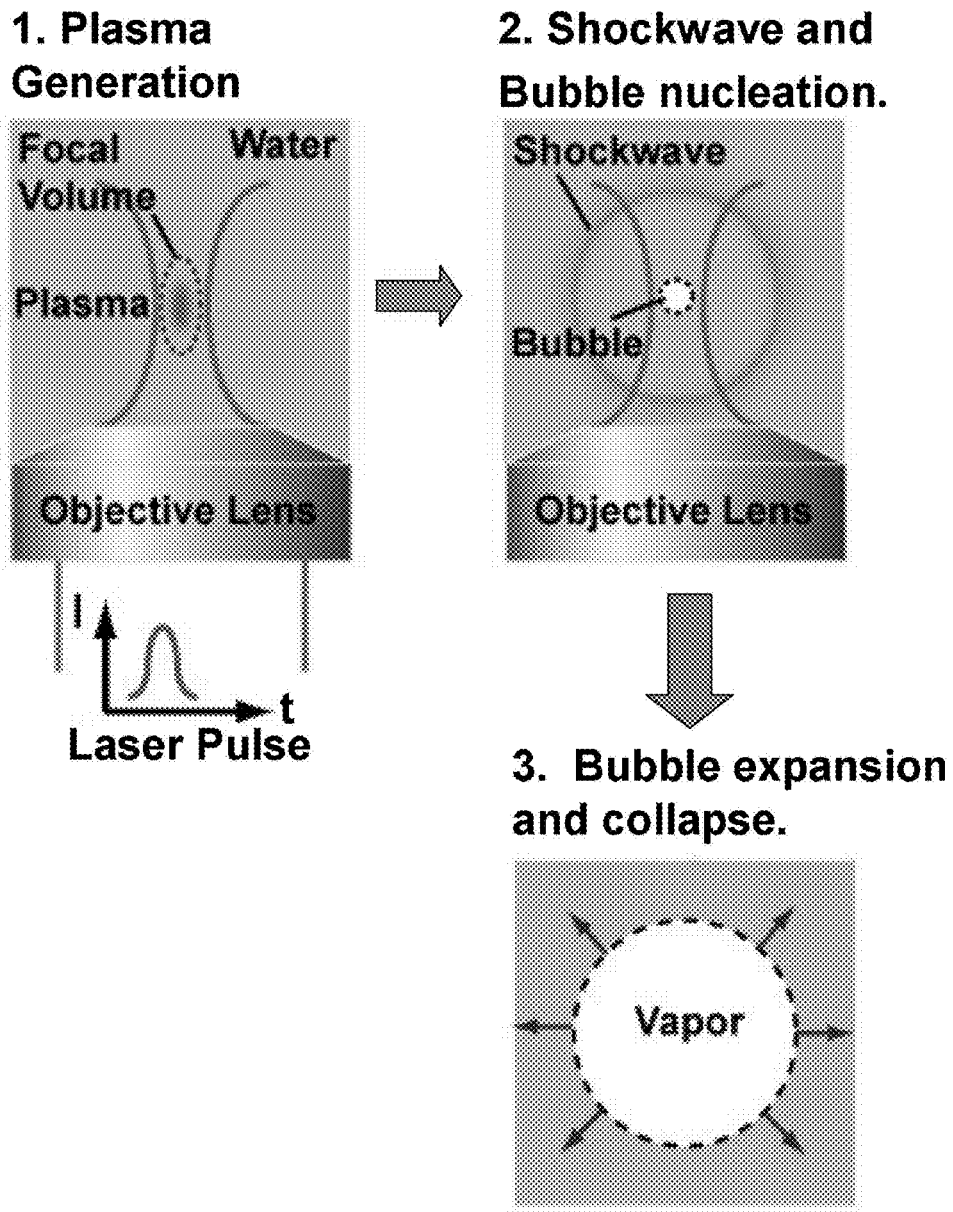
FIGS. 1A and 1B depicts the process of creating a cavitation bubble using a pulsed laser.
Figure 1B:
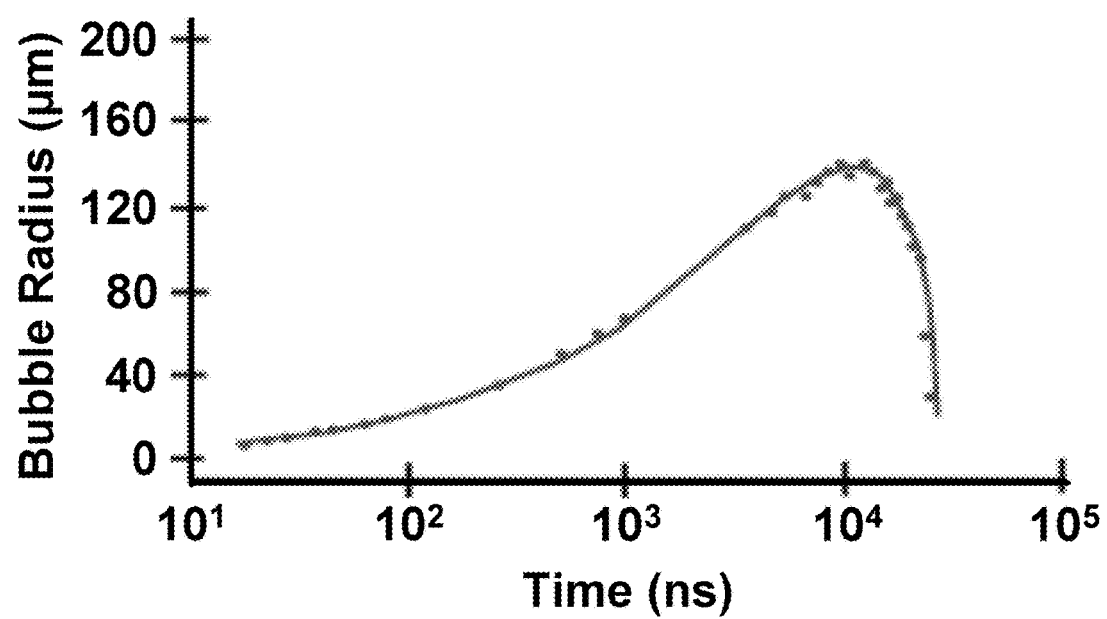

FIG. 1A illustrates the underlying mechanism of laser pulse induced cavitation bubble formation in aqueous media. A laser pulse is focused on a specified volume of the aqueous medium. Absorption of this optical energy results in a breakdown of water molecules within the area of focus, generating a plasma bubble near the focal point. The components of the plasma recombine in a few nanoseconds, generating a shockwave of released energy and an explosive vapor bubble (also referred to as a cavitation bubble) that expands as rapidly as 100 meters per second followed by a rapid collapse. FIG. 1B shows a typical time course for bubble formation and collapse. Bubble radius can be seen to increase rapidly up to approximately 1 microsecond following initiation, followed by a rapid collapse.

Figure 2:
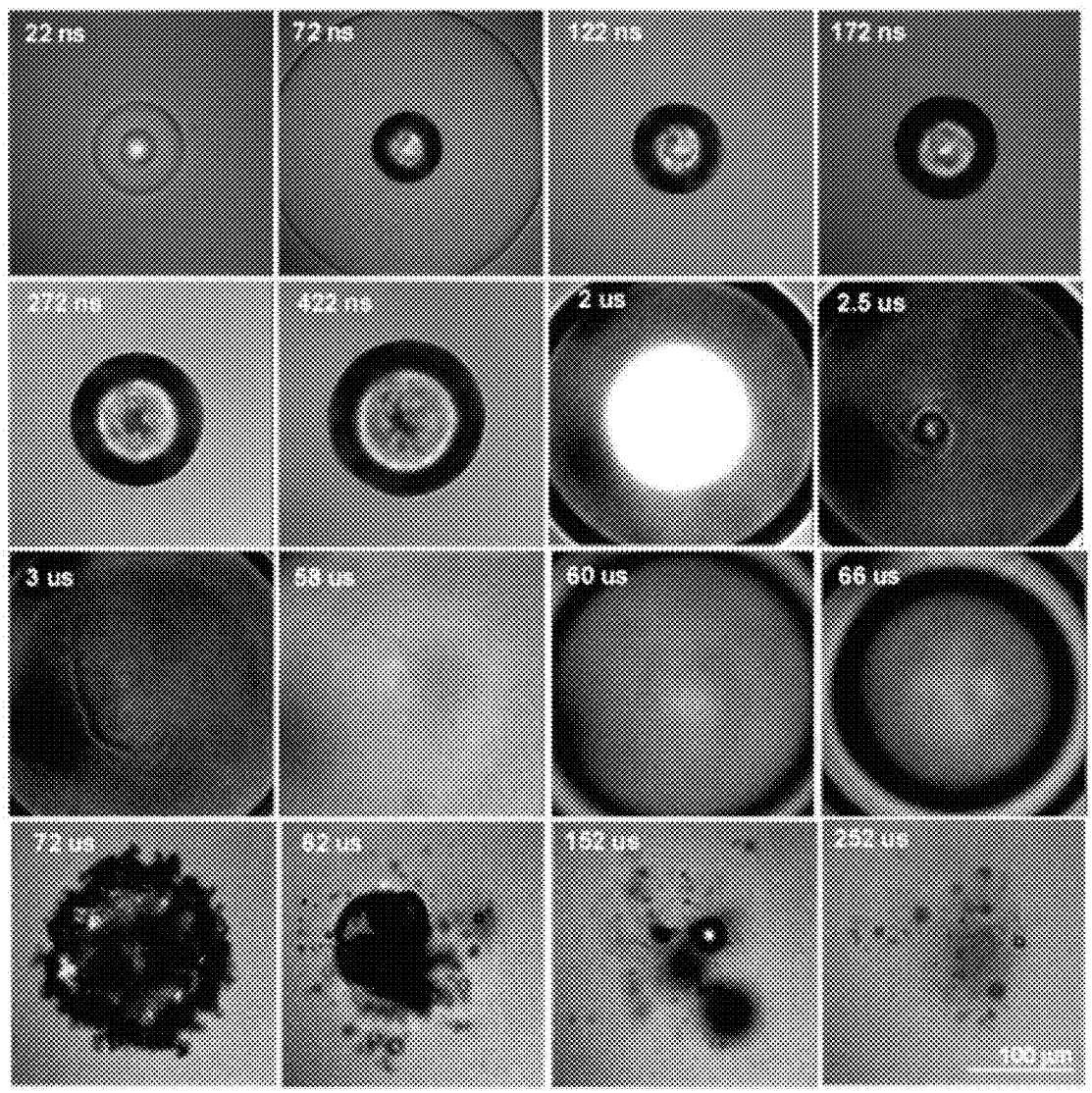
FIG. 2 illustrates the time course of formation and subsequent collapse of a cavitation bubble generated using a pulsed laser.

FIG. 2 shows a series of photomicrographs of bubble formation using this actuation mechanism. A shockwave can be seen expanding outwards from the point of plasma generation at 22 nanoseconds following initiation. A rapidly expanding cavitation bubble is readily observable at 72 nanoseconds, with the bubble expanding out of the frame by 55 microseconds. This is followed by a rapid collapse of the bubble, which is essentially complete by 152 microseconds following initiation. The pressure inside such a bubble can be as high as tens of megapascals or more as the bubble expands. A number of unique properties, such as rapid actuation of the driving force (femtoseconds to nanoseconds, depending on laser pulse duration), rapid conversion of the directed energy into mechanical power, the large magnitude of the resulting forces, the relatively large displacement produced by the cavitation bubble, and the extremely transient nature of the forces involved provide a unique mechanism for ultrafast micro- and nano-fluidic actuation. Utilizing this actuation mechanism, micro- and nano-fluidic components such as switches, valves, and pumps can be realized to guide, drive, and regulate fluid flows at micro- and nano-fluidic scales with unprecedented speed and accuracy, thereby enabling novel functionalities.

Figure 3:
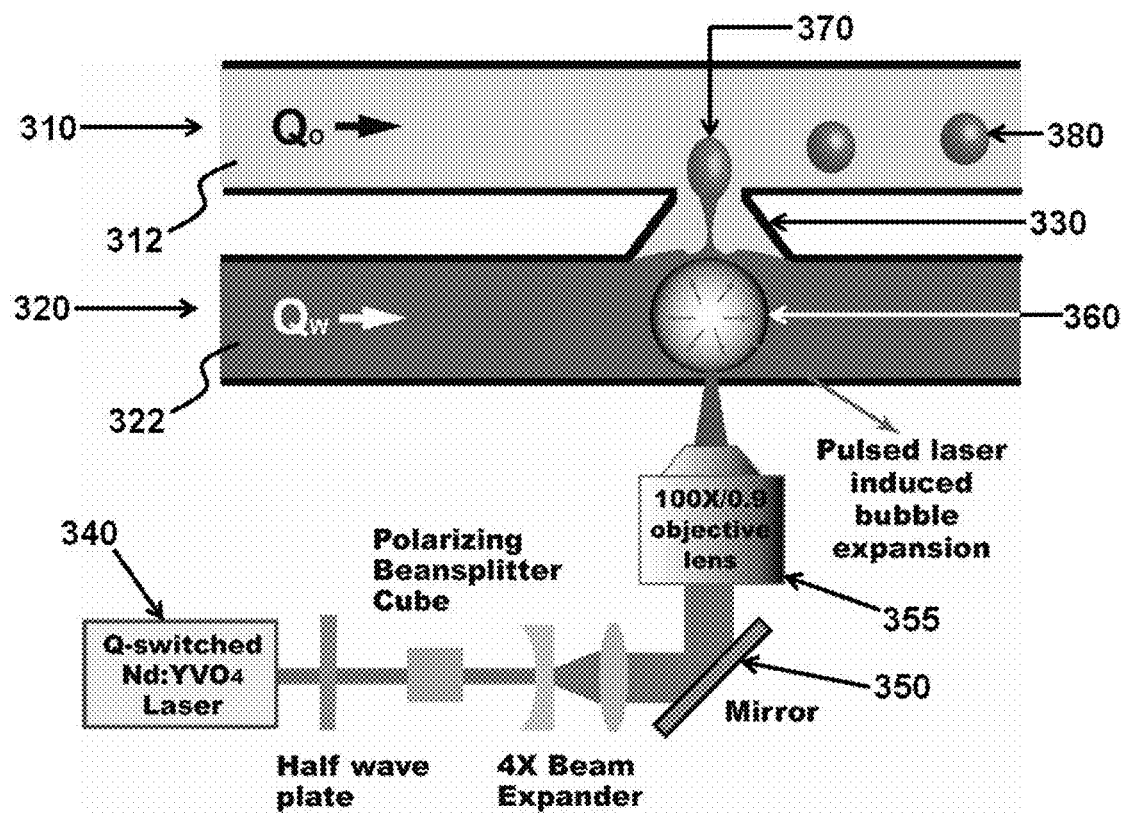
FIG. 3 schematically illustrates generation of droplets within a fluid channel in accordance with one embodiment of the invention.

One illustrative embodiment of the invention is shown schematically in FIG. 3. The figure shows a device, which can be a microfluidic device, comprising a first fluid channel (320) (e.g., a microchannel) containing a first fluid (312) and a second fluid channel (310) (e.g., a microchannel) containing a second fluid (322) where the second fluid is immiscible in the first fluid and where the fluid channels are in fluid communication with each other via an opening (330). In some embodiments this opening is in the form of a nozzle. A directed energy source (340), for example a pulse laser, is directed towards the first fluid channel (320). In certain embodiments, the laser can be directed using, for example, a mirror (350) and focused into a volume of the first fluid channel (320) using a lens (355). In some embodiments the mirror and/or the lens are configured to permit focusing of the directed energy source at different positions within the first fluid channel (320). The directed energy source (340) initiates the formation of a transient bubble (360) (e.g., a cavitation bubble) within the first fluid channel (320), driving a droplet of the first fluid (370) into the second fluid channel (310). Collapse of the bubble causes a back flow of the extruded first fluid, causing the formation of a narrow "neck" and quickly leading to the release the droplet (380) into the second fluid channel (310).

Figure 8:
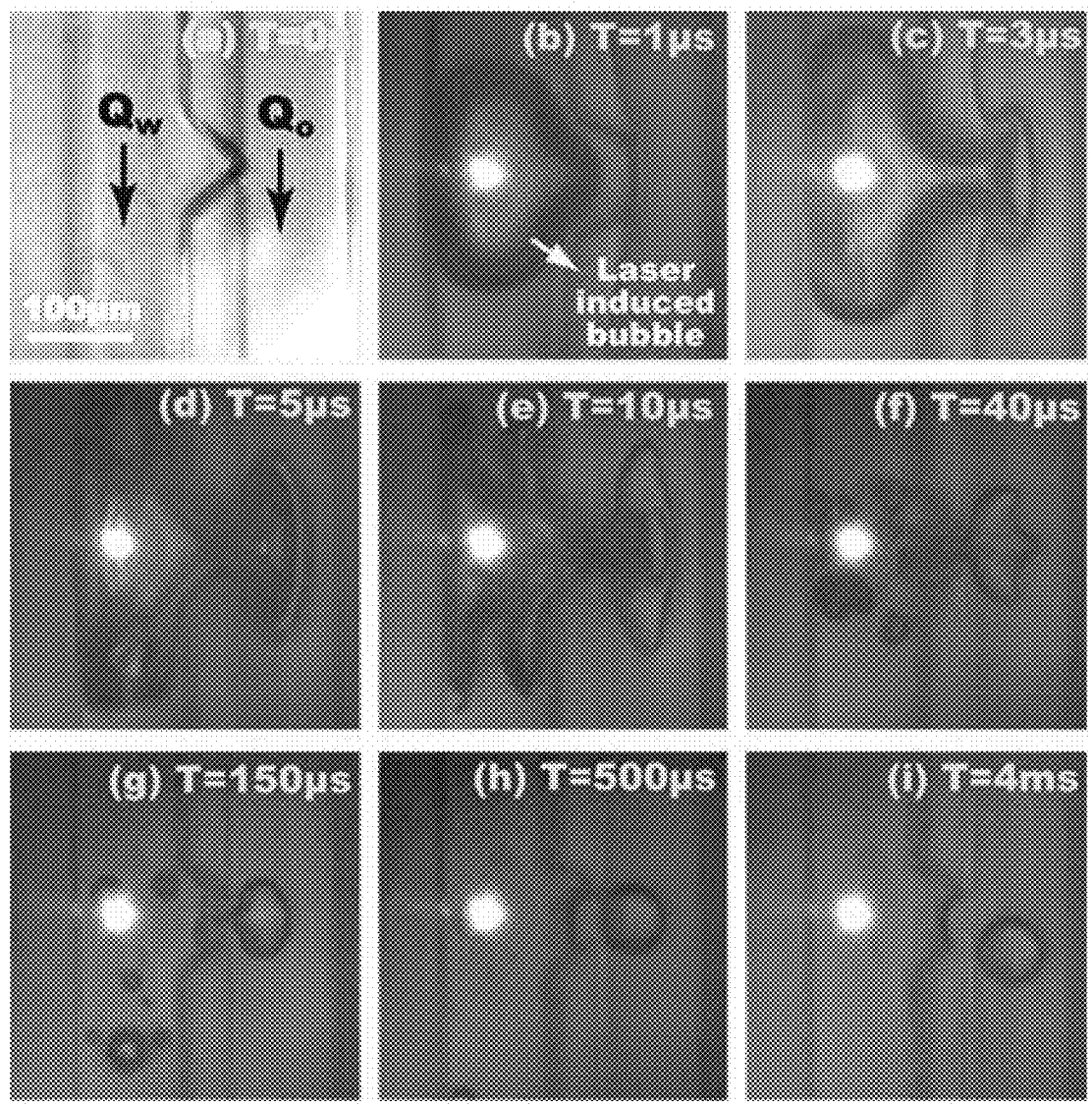
FIG. 8, panels (a)-(i), show a time-resolved image series of on-demand droplet generation.

A series of photographs showing the formation and release of a droplet in such a device is shown in FIG. 8. FIG. 8, panel (a), shows a set of parallel fluid channels connected by an opening. Induction of a cavitation bubble is seen in FIG. 8, panel (b), which extrudes a portion of the contents of one channel into the other as can be seen in FIG. 8, panels (c) to (e). As the bubble collapses a narrow "neck" of connecting fluid is formed, as seen in FIG. 8, panels (f) and (g). Finally, this neck retracts and the droplet is released as shown in FIG. 8, panels (h) and (i).

Figure 4:
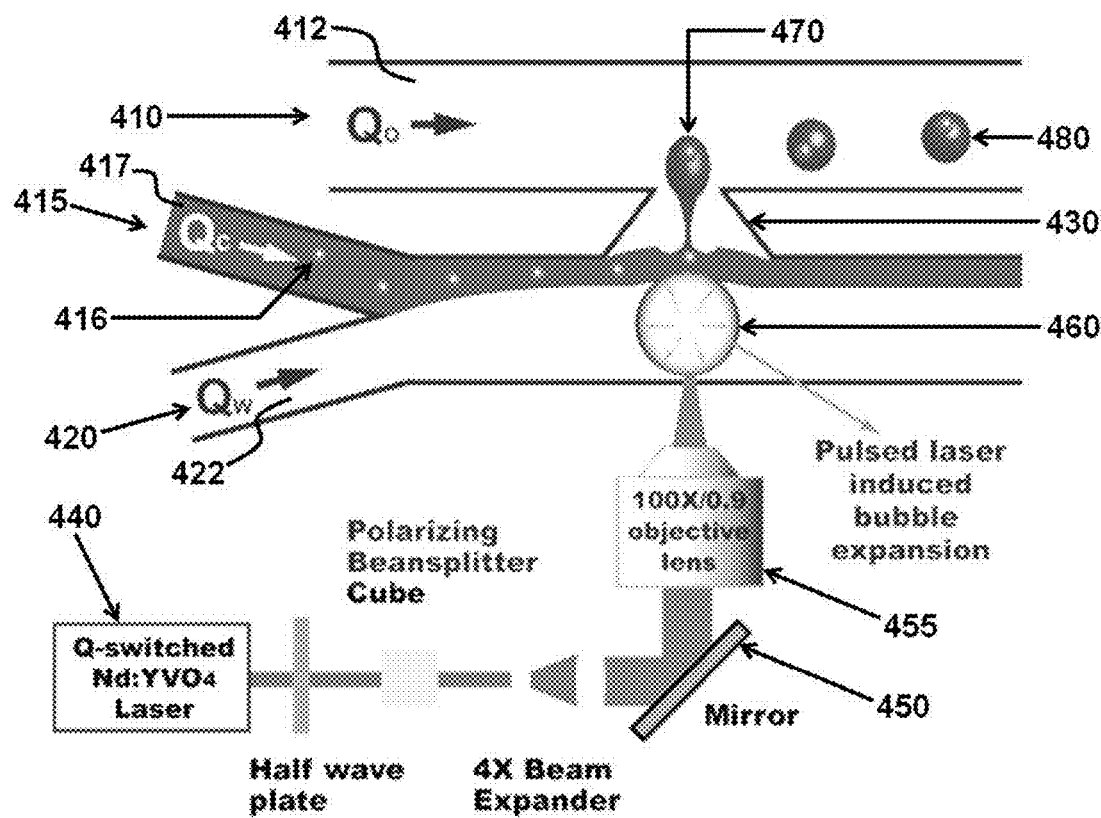
FIG. 4 schematically illustrates generation of droplets that incorporate particles or cells within a fluid channel in accordance with another embodiment of the invention.

Another embodiment of the invention is shown in FIG. 4. The figure shows a device, which can be a microfluidic device, comprising a first fluid channel (420) (e.g., a microchannel) containing a first fluid, a second fluid channel (415) (e.g., a microchannel) containing a second fluid (417), and a third fluid channel (410) (e.g., a microchannel) containing a third fluid (412) where the second fluid is immiscible in the third fluid and where the second fluid channel and the third fluid channel are in fluid communication with each other via an opening (430). In some embodiments this opening is in the form of a nozzle. In certain embodiments the second fluid may include particles or cells (416), and can be immiscible in the first fluid by virtue of laminar flow and/or by virtue of chemical immiscibility. A directed energy source (440), for example a pulse laser, is directed towards the first fluid channel (420), optionally using a mirror (450) and directed, and optionally focused, into a volume of the first fluid channel (420) using, for example, a lens (455). In some embodiments the mirror and/or the lens are configured to permit focusing of the directed energy source at different positions within the first fluid channel (420). The directed energy source (440) initiates the formation of a transient bubble (460) (e.g., a cavitation bubble) within the first fluid channel (420), driving a droplet of the second fluid (470) into the third fluid channel (410). Collapses of the bubble causes a back flow of the extruded second fluid, causing the formation of a narrow "neck" and quickly leading to the release the droplet (480) into the third fluid channel (410).

Figure 5:
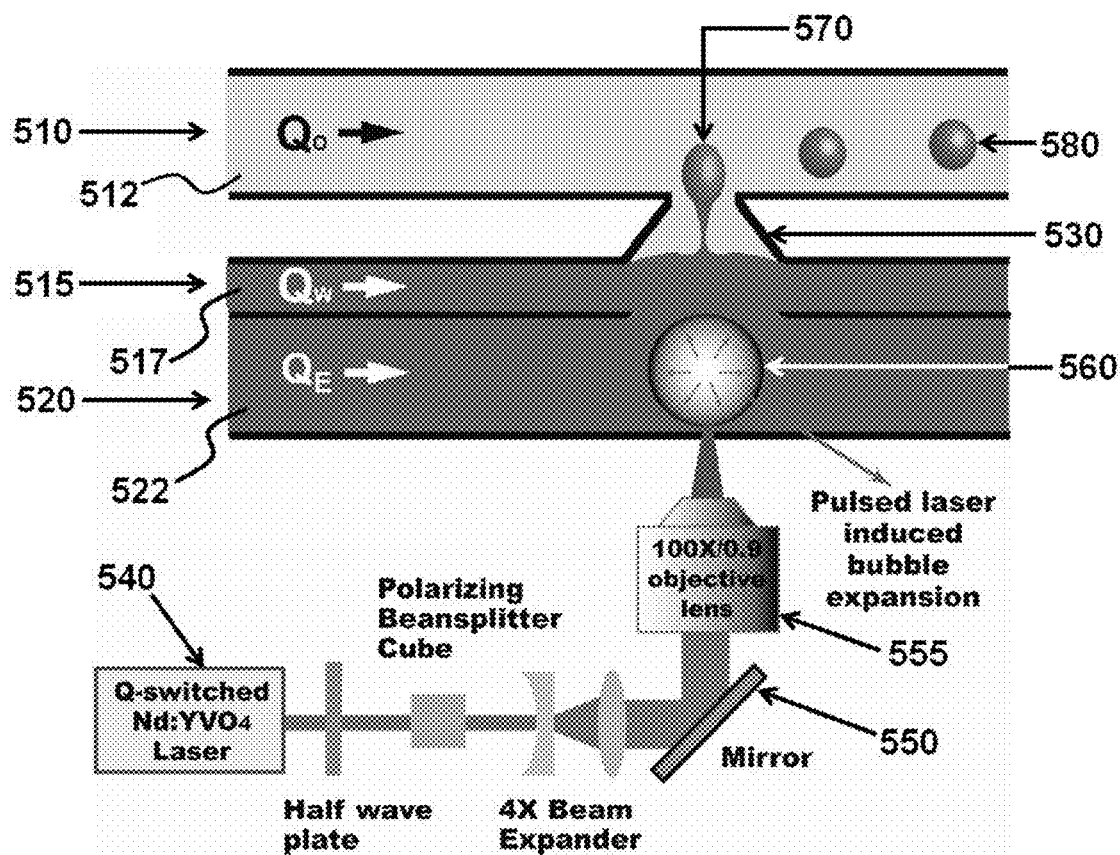
FIG. 5 schematically illustrates generation of droplets within a fluid channel in accordance with another embodiment of the invention.

Another illustrative embodiment is shown in FIG. 5. The figure shows a device, which can be a microfluidic device, comprising a first fluid channel (520) (e.g., a microchannel) containing a first fluid (522), a second fluid channel (515) (e.g., a microchannel) containing a second fluid (517), and a third fluid channel (510) (e.g., a microchannel) containing a third fluid (512) where the second fluid is immiscible in the third fluid and where the second fluid channel and the third fluid channel are in fluid communication with each other via an opening (530). In some embodiments this opening is in the form of a nozzle. The second fluid may include particles or cells (516) that may be subsequently encapsulated in the generated fluid droplet, and can be in fluid communication with the first fluid channel (520) via an aperture (535) or similar structure. A directed energy source (540), for example a pulse laser, is directed towards the first fluid channel (520), optionally using a mirror (550), and directed (and optionally focused) into a volume of the first fluid channel (520) using, for example, a lens (555). In some embodiments the mirror and/or the lens are configured to permit focusing of the directed energy source at different positions within the first fluid channel (520). The directed energy source (540) initiates the formation of a transient bubble (560) (e.g., a cavitation bubble) within the first fluid channel (520), driving a droplet of the second fluid (570) into the third fluid channel (510). Collapse of the bubble causes a back flow of the extruded second fluid, causing the formation of a narrow "neck" and quickly leading to the release the droplet (580) into the third fluid channel (510).

Figure 6:
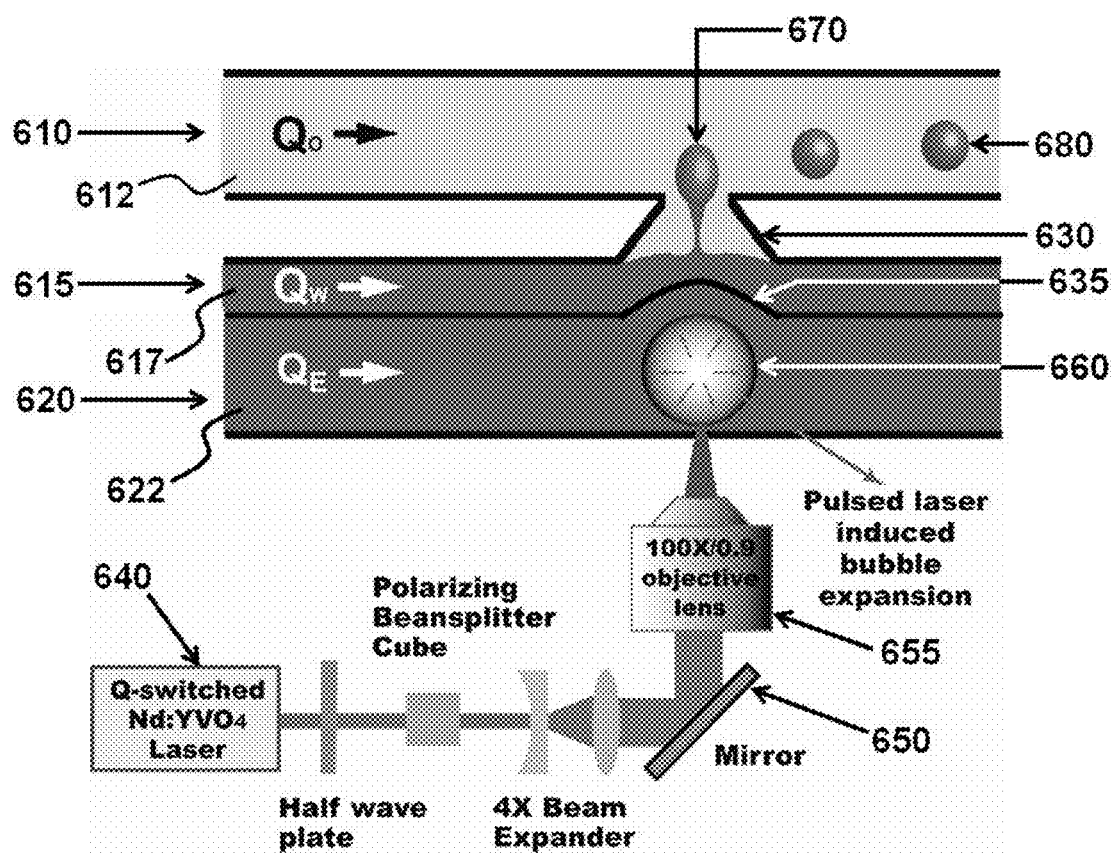
FIG. 6 schematically illustrates generation of droplets within a fluid channel in accordance with another embodiment of the invention.

Another embodiment of the invention is shown in FIG. 6. The figure shows a device, which can be a microfluidic device, comprising a first fluid channel (620) (e.g., a microchannel) containing a first fluid (622), a second fluid channel (615) (e.g., a microchannel) containing a second fluid (617), and a third fluid channel (610) (e.g., a microchannel) containing a third fluid (612) where the second fluid is immiscible in the third fluid and where the second fluid channel and the third fluid channel are in fluid communication with each other via an opening (630). In some embodiments this opening is in the form of a nozzle. A flexible membrane (635) is interposed between the first fluid channel (620) and the second fluid channel (615). A directed energy source (640), for example a pulse laser, is directed towards the first fluid channel (520), optionally using a mirror (650) and focused into a volume of the first fluid channel (620) optionally using a lens (655). In some embodiments the mirror and/or the lens are configured to permit focusing of the directed energy source at different positions within the first fluid channel (620). The directed energy source (640) initiates the formation of a transient bubble (660) (e.g., a cavitation bubble) within the first fluid channel (620), which results in an elastic deformation of the flexible membrane (635). This elastic deformation drives a droplet of the second fluid (670) into the third fluid channel (610). Reversal of the elastic deformation following collapse of the bubble (660) results in a back flow of the extruded second fluid, causing the formation of a narrow "neck" and quickly leading to the release the droplet (680) into the third fluid channel (610). Response time of this configuration can be controlled by the stiffness of the elastic membrane in addition to the other parameters discussed above.

Figure 7:
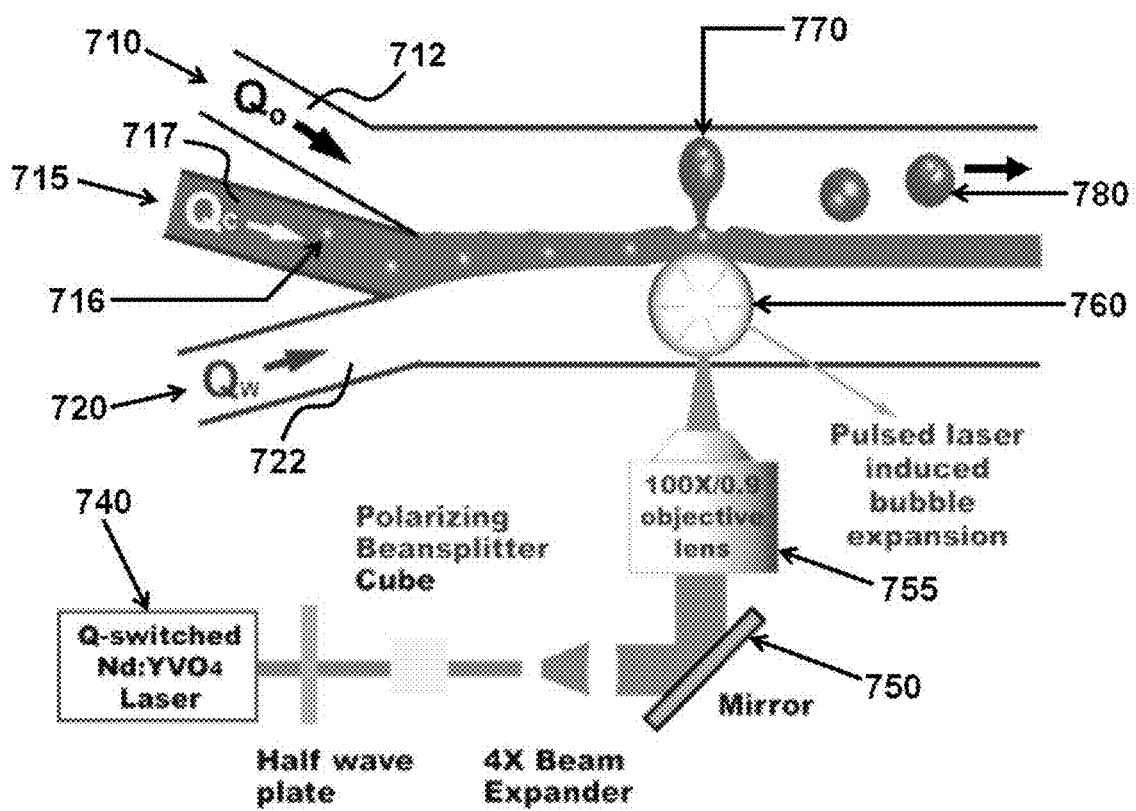
FIG. 7 schematically illustrates generation of droplets that incorporate particles or cells within a fluid channel in accordance with another embodiment of the invention.

Yet another embodiment of the invention is shown in FIG. 7. The figure shows a device, which can be a microfluidic device, comprising a first fluid channel (720) (e.g., a microchannel) containing a first fluid (720), a second fluid channel (715) (e.g., a microchannel) containing a second fluid (717), and a third fluid channel (710) (e.g., a microchannel) containing a third fluid (712) wherein the first, second, and third fluids are immiscible (e.g., by virtue of laminar flow and/or chemical immiscibility). The second fluid may include particles or cells (716) that may be subsequently encapsulated in the generated fluid droplet. A directed energy source (740), for example a pulse laser, is directed towards the first fluid channel (720), optionally using a mirror (750), and focused into a volume of the first fluid channel (720), optionally using a lens (755). In some embodiments the mirror and/or the lens are configured to permit focusing of the directed energy source at different positions within the first fluid channel (720). The directed energy source (740) initiates the formation of a transient bubble (760) (e.g., a cavitation bubble) within the first fluid channel (720), driving a droplet of the second fluid (770) into the third fluid channel (710). Collapse of the bubble causes a back flow of the extruded second fluid, causing the formation of a narrow "neck" and quickly leading to the release the droplet (780) into the third fluid channel (710).

While use of a pulse laser as a directed energy source has been noted above, it should be noted that other energy sources are suitable for use with the invention. Alternative directed energy sources include non-laser, high output optical sources (e.g. focused arc lamps), microwave irradiation, inductive heating, and acoustic energy (e.g. ultrasound).

In certain embodiments, pulsed lasers are preferred energy sources. Lasers are advantageous in that they do not require any electrical or mechanical wiring or interconnects to deliver energy. A laser beam can be focused to any arbitrary 3D location across a transparent substrate. This eliminates the interfacing problems and facilitates the integration on standard foundry microfluidic chips.

Illustrative lasers include, but are not limited to nanosecond pulsed laser with a wavelength, for example, at 532 nm. Microsecond, picosecond or femtosecond pulse lasers, and the like, can also be applied. In certain embodiments the wavelength of laser can also in the UV, visible light, or near infrared.

In certain embodiments the devices or systems comprising the devices can incorporate a monitoring device that characterizes the contents of one or more of the fluid channels. Data from this monitoring device can be transmitted to a controller, which in turn may be configured to trigger the directed energy source based on data received from the monitor. For example, a fluorescence monitor may by aligned with a fluid channel that contains fluorescently labeled cells or particles. When data from the monitor indicates that a cell containing the desired fluorescent label is aligned with droplet generating mechanism, the controller can initiate a laser pulse that results in the formation of a droplet that encapsulates the desired cell. Similarly, absorbance may be used to differentiate contents of a monitored fluid stream. This arrangement advantageously permits selection of specific volumes within a fluid channel that may have unique or desirable contents for transfer to a second fluid channel for collection or distribution to another functional area of the device. Monitors are not limited to fluorescence or absorbance monitors. For example, magnetic monitors, capacitance monitors, inductance monitors, electrochemical monitors can similarly be used to advantage.

It will be noted that while in certain embodiments, one or more of the fluid streams (e.g., fluid paths) may be confined within physical channels (e.g., microchannels), the fluid streams need not be constrained or separated by a physical barrier/channel wall. In certain embodiments fluid streams can be confined and/or separated, and/or directed along predetermined paths by variations in the polarity/hydrophobicity/surface free energy of the surface upon which they are disposed (see, e.g., Zhao et al. (2002) *Anal. Chem.,* 74(16): 4259-4268), by the use of electrowetting techniques (see, e.g., Cheng and Hsiung (2004) *Biomedical Microdevices,* 6(5): 341-347), by electrokinetic means, by the use of directed laminar flow (e.g., by adjusting flow rates, and/or stream cross-section, and/or stream viscosity), and the like.

In certain embodiments, the fluid streams are microfluid streams. A "microfluid stream" refers to a stream wherein at least about 40%, or at least about 50%, or at least about 60%, or at least about 70%, or at least about 80%, or at least about 90%, or at least about 95%, or at least about 98%, or at least about 99%, of the flux or mass of said fluid stream passes through a cross-sectional area having at least one characteristic dimension (e.g., width or diameter) less than 1,000 µm, more preferably less than about 900 µm, or less than about 800 µm, or less than about 700 µm, or less than about 600 µm, or less than about 500 µm, or less than about 400 µm, or less than about 300 µm, or less than about 250 µm, or less than about 200 µm, or less than about 150 µm, or less than about 100 µm, or less than about 75 µm, or less than about 50 µm, or less than about 40 µm, or less than about 30 µm, or less than about 20 µm, or less than about 10 µm, or less than about 1 µm. In certain embodiments the "microfluid stream" refers to a fluid stream contained within a microfluidic channel.

In certain embodiments one or more of the fluid streams are disposed in a channel or a microchannel. The terms "microfluidic channel" or "microchannel" are used interchangeably and refer to a channel having at least one characteristic dimension (e.g., width or diameter) less than 1,000 µm, more preferably less than about 900 µm, or less than about 800 µm, or less than about 700 µm, or less than about 600 µm, or less than about 500 µm, or less than about 400 µm, or less than about 300 µm, or less than about 250 µm, or less than about 200 µm, or less than about 150 µm, or less than about 100 µm, or less than about 75 µm, or less than about 50 µm, or less than about 40 µm, or less than about 30 µm, or less than about 20 µm.

In certain embodiments the methods and devices described herein may utilize immiscible fluids. In this context, the term "immiscible" when used with respect to two fluids indicates that the fluids when mixed in some proportion, do not form a solution. Classic immiscible materials are water and oil. Immiscible fluids, as used herein also include fluids that substantially do not form a solution when combined in some proportion. Commonly the materials are substantially immiscible when they do not form a solution if combined in equal proportions. In certain embodiments immiscible fluids include fluids that are not significantly soluble in one another, fluids that do not mix for a period of time due to physical properties such as density or viscosity, and fluids that do not mix for periods of time due to laminar flow.

In addition, such fluids are not restricted to liquids but may include liquids and gases. Thus, for example, where the droplets are to be formed comprising an aqueous solvent (such as water) any number of organic compounds such as carbon tetrachloride, chloroform, cyclohexane, 1,2-dichloroethane, dichloromethane, diethyl ether, dimethyl formamide, ethyl acetate, heptane, hexane, methyl-tert-butyl ether pentane, toluene, 2,2,4-trimethylpentane, and the like are contemplated. Various mutually insoluble solvent systems are well known to those skilled in the art (see e.g. Table 1). In another example, droplets of aqueous buffer containing physiologically normal amounts of solute may be produced in a dense aqueous buffer containing high concentrations of sucrose. In yet another example, droplets of an aqueous buffer containing physiologically normal amounts of solute may be produced in a second aqueous buffer containing physiologically normal amounts of solute where the two buffers are segregated by laminar flow. In still another example, droplets of a fluid may be produced in a gas such as nitrogen or air.

Table 1 illustrates various solvents that are either miscible or immiscible in each other. The solvent on left column does not mix with solvents on right column unless otherwise stated.

| Solvents | Immiscibility |
| --- | --- |
| Acetone | can be mixed with any of the solvents listed in the column at left |
| Acetonitrile | cyclohexane, heptane, hexane, pentane, 2,2,4-trimethylpentane |
| carbon tetrachloride | can be mixed with any of the solvents listed in the column at left except water |
| chloroform | can be mixed with any of the solvents listed in the column at left except water |
| cyclohexane | acetonitrile, dimethyl formamide, dimethyl sulfoxide, methanol, water |
| 1,2-dichloroethane | can be mixed with any of the solvents listed in the column at left except water |
| dichloromethane | can be mixed with any of the solvents listed in the column at left except water |
| diethyl ether | dimethyl sulfoxide, water |
| dimethyl formamide | cyclohexane, heptane, hexane, pentane, 2,2,4-trimethylpentane, water |
| dimethyl solfoxide | cyclohexane, heptane, hexane, pentane, 2,2,4-trimethylpentane, diethyl ether |
| 1,4-dioxane | can be mixed with any of the solvents listed in the column at left |
| ethanol | can be mixed with any of the solvents listed in the column at left |
| ethyl acetate | can be mixed with any of the solvents listed in the column at left except water |
| heptane | acetonitrile, dimethyl formamide, dimethyl sulfoxide, methanol, water |
| hexane | acetonitrile, dimethyl formamide, dimethyl sulfoxide, methanol, acetic acid, water |
| methanol | cyclohexane, heptane, hexane, pentane, 2,2,4-trimethylpentane |
| methyl-tert-butyl ether | can be mixed with any of the solvents listed in the column at left except water |
| pentane | acetonitrile, dimethyl formamide, dimethyl sulfoxide, methanol, water, acetic acid |
| 1-propanol | can be mixed with any of the solvents listed in the column at left |
| 2-propanol | can be mixed with any of the solvents listed in the column at left |
| tetrahydrofuran | can be mixed with any of the solvents listed in the column at left |
| toluene | can be mixed with any of the solvents listed in the column at left except water |

| Solvents | Immiscibility |
|---|---|
| 2,2,4-trimethylpentane | acetonitrile, dimethyl formamide, dimethyl sulfoxide, methanol, water |
| water | carbon tetrachloride, chloroform, cyclohexane, 1,2-dichloroethane, dichloromethane, diethyl ether, dimethyl formamide, ethyl acetate, heptane, hexane, methyl-tert-butyl ether, pentane, toluene, 2,2,4-trimethylpentane |

In certain embodiments the first fluid and second fluid need not be immiscible in each other. In such embodiments, injected droplets can be kept separate from each other simply by adjusting flow rates in the microchannels and rate of bubble formation to form separated bubbles.

In various embodiments the droplets generated by the devices and methods described herein can contain or encapsulate a wide variety of materials. In some embodiments the droplets may contain test samples, cells, organelles, proteins, nucleic acids, enzymes, PCR or other testing reagents, biochemicals, dyes, or particulates (for example polymeric microspheres, metallic microparticles, or pigments). In still other embodiments a droplet may encapsulate one or more previously generated droplets. In addition, the invention need not be limited to aqueous droplet systems. For example, such droplet generating methods and devices may be used in nanoparticle coating, where materials in organic solvents can be used to deposit layers on or encapsulate nanoparticles.

As noted above, in some embodiments an opening in a fluid channel can be configured as a nozzle. The depth, inner diameter, and outer diameter of such a nozzle can be optimized to control droplet size, droplet uniformity, mixing at the fluid interface, or a combination of these.

The droplet generation devices described herein may be provided on a substrate that differs from the material that comprises the fluid channels. For example, the fluid channels may be fabricated using an elastomeric material that is disposed upon a rigid surface. Suitable fluid channel materials include but are not limited to flexible polymers such as PDMS, plastics, and similar materials. Fluid channels may also be comprised of nonflexible materials such as rigid plastics, glass, silicon, quartz, metals, and similar material. Suitable substrates include but are not limited to transparent substrates such as polymers, plastic, glass, quartz, or other dielectric materials. Other suitable substrate materials include but are not limited to nontransparent materials such as opaque or translucent plastics, silicon, metal, ceramic, and similar materials.

The parameters described above and in the Examples (e.g., flow rate(s), laser intensity, laser frequency/wavelength, channel dimensions, port/nozzle dimensions, channel wall stiffness, location of cavitation bubble formation, and the like) can be varied to optimize droplet formation and/or droplet/particle/cell encapsulation for a particular desired application.

There are a number of formats, materials, and size scales that may be used in the construction of the droplet generating devices described herein and in microfluidic devices that may incorporate them. In some embodiments the droplet generating devices and the connecting fluid channels are comprised of PDMS (or other polymers), and fabricated using soft lithography. PDMS is an attractive material for a variety of reasons, including but not limited to low cost, optical transparency, ease of molding, and elastomeric character. PDMS also has desirable chemical characteristics, including compatibility with both conventional siloxane chemistries and the requirements of cell culture (e.g. low toxicity, gas permeability). In an illustrative soft lithography method, a master mold is prepared to form the fluid channel system. This master mold may be produced by a micromachining process, a photolithographic process, or by any number of methods known to those with skill in the art. Such methods include, but are not limited to, wet etching, electron-beam vacuum deposition, photolithography, plasma enhanced chemical vapor deposition, molecular beam epitaxy, reactive ion etching, and/or chemically assisted ion beam milling (Choudhury (1997) *The Handbook of Microlithography, Micromachining, and Microfabrication,* Soc. Photo-Optical Instru. Engineer.; Bard & Faulkner, *Fundamentals of Microfabrication*).

Once prepared the master mold is exposed to a propolymer, which is then cured to form a patterned replica in PDMS. The replica is removed from the master mold, trimmed, and fluid inlets are added where required. The polymer replica may be optionally be treated with a plasma (e.g. an $O_2$ plasma) and bonded to a suitable substrate, such as glass. Treatment of PDMS with $O_2$ plasma generates a surface that seals tightly and irreversibly when brought into conformal contact with a suitable substrate, and has the advantage of generating fluid channel walls that are negatively charged when used in conjunction with aqueous solutions. These fixed charges support electrokinetic pumping that may be used to move fluid through the device. While the above described fabrication of a droplet generating device using PDMS, it should be recognized that numerous other materials can be substituted for or used in conjunction with this polymer. Examples include, but are not limited to, polyolefin plastomers, perfluoropolyethylene, polyurethane, polyimides, and cross-linked phenol/formaldehyde polymer resins.

In some embodiments single layer devices are contemplated. In other embodiments multilayer devices are contemplated. For example, a multilayer network of fluid channels may be designed using a commercial CAD program. This design may be converted into a series of transparencies that is subsequently used as a photolithographic mask to create a master mold. PDMS cast against this master mold yields a polymeric replica containing a multilayer network of fluid channels. This PDMS cast can be treated with a plasma and adhered to a substrate as described above.

As noted above, the methods and devices described herein are particularly suitable for use in microfluidic devices. In some embodiments therefore the fluid channels are microchannels. Such microchannels have characteristic dimensions ranging from about 100 nanometers to 1 micron up to about 500 microns. In various embodiments the characteristic dimension ranges from about 1, 5, 10, 15, 20, 25, 35, 50 or 100 microns up to about 150, 200, 250, 300, or 400 microns. In some embodiments the characteristic dimension ranges from about 20, 40, or about 50 microns up to about 100, 125, 150, 175, or 200 microns. In various embodiments the wall thickness between adjacent fluid channels ranges from about 0.1 micron to about 50 microns, or about 1 micron to about 50 microns, more typically from about 5 microns to about 40 microns. In certain embodiments the wall thickness between adjacent fluid channels ranges from about 5 microns to about 10, 15, 20, or 25 microns.

In various embodiments the depth of a fluid channel ranges from 5, 10, 15, 20 microns to about 1 mm, 800 microns, 600 microns, 500 microns, 400 microns, 300 microns, 200 microns, 150 microns, 100 microns, 80 microns, 70 microns, 60 microns, 50 microns, 40 microns, or about 30 microns. In certain embodiments the depth of a fluid channel ranges from about 10 microns to about 60 microns, more preferably from about 20 microns to about 40 or 50 microns. In some embodiments the fluid channels can be open; in other embodiments the fluid channels may be covered.

As noted above, some embodiments of the invention include a nozzle. Where a nozzle is present, the nozzle diameter can range from about 0.1 micron, or about 1 micron up to about 300 microns, 200 microns, or about 100 microns. In certain embodiments the nozzle diameter can range from about 5, 10, 15, or 20 microns up to about 25, 30, 35, 40, 45, 50, 55, 60, 65, 70, 75, or about 80 microns. In some embodiments the nozzle diameter ranges from about 1, 5, 10, 15, or 20 microns to about 25, 35, or 40 microns.

In some embodiments the methods and devices described herein can generate droplets at a rate ranging from zero droplets/sec, about 2 droplets/sec, about 5 droplets/sec, about 10 droplets/sec, about 20 droplets/sec, about 50 droplets/sec, about 100 droplets/sec, about 500 droplets/sec, or about 1000 droplets/sec, up to about 1,500 droplets/sec, about 2,000 droplets/sec, about 4,000 droplets/sec, about 6,000 droplets/sec, about 8,000 droplets/sec, about 10,000 droplets/sec, about 20,000 droplets/sec, about 50,000 droplets/sec, and about 100,000 droplets/sec.

In various embodiments the devices and methods described herein can generate droplets having a substantially continuous volume. Droplet volume can be controlled to provide volumes ranging from about 0.1 fL, about 1 fL, about 10 fL, and about 100 fL to about 1 microliter, about 500 nL, about 100 nL, about 1 nL, about 500 pL or about 200 pL. In certain embodiments volume control of the droplet ranges from about 1 pL to about 150 pL, about 200 pL, about 250 pL, or about 300 pL.

As indicate above, the microchannel droplet formation/injection devices described herein can provide a system integrated with other processing modules on a microfluidic "chip" or in flow through fabrication systems for microparticle coating, microparticle drug carrier formulation, and the like. These uses, however, are merely illustrative and not limiting.

In various embodiments microfluidic that incorporate components/modules/devices that performing the methods described herein can can manipulate volumes as small as one to several nanoliters. Because the microfluidic reaction volume is close to the size of single mammalian cells, material loss is minimized in single-cell mRNA analysis with these devices. The ability to process live cells inside microfluidic devices provides a great advantage for the study of single-cell transcriptomes because mRNA is rapidly degraded with cell death. One illustrative highly integrated microfluidic device, having 26 parallel 10 nL reactors for the study of gene expression in single human embryonic stem cells (hESC) has been reported (Zhong et al. (2008) *Lab on a Chip,* 8: 68-74; Zhong et al. (2008) *Curr. Med. Chem.,* 15: 2897-2900) and can be easily modified to intetrate the devices described herein. Certain illustrative microfluidic devices include systems for obtaining single-cell cDNA including cell capture, mRNA capture/purification, cDNA synthesis/purification, are performed inside the device. The present devices and methods offer effective means of encapsulating and and/or separating individual cells for, e.g., further processing, in such devices.

Any of a number of approaches can be used to convey the fluids, or mixtures of droplets, particles, cells, etc. along the flow paths and/or channels of the devices described herein. Such approaches include, but are not limited to gravity flow, syringe pumps, peristaltic pumps, electrokinetic pumps, bubble-driven pumps, and air pressure driven pumps.

EXAMPLES

The following examples are offered to illustrate, but not to limit the claimed invention.

Example 1

Droplet Generation Driven by Pulse-Laser Induced Cavitation

A pulse laser-driven droplet generation (PLDG) device as shown in FIG. 3 was constructed using standard soft lithography techniques. The PLDG device had two fluid channels, one filled with water and the other with oil. Both fluid channels were 100 microns in width and 100 microns in height. The fluid channels were connected with an opening configured as a nozzle, with a neck that was 30 microns in width. Flow rates in the channels were adjusted to produce a stable oil/water interface.

The actuation of this PLDG device was based on a laser pulse-induced cavitation bubble, generated when an intense laser pulse was focused into the water containing fluid channel. Plasma formation at the focal point of the laser pulse generates a rapidly expanding cavitation bubble, as described above. This perturbs the oil/water interface and pushes a droplet of water into the neighboring oil-filled fluid channel to from stable water droplets. The lifetime of this cavitation bubble ranged from tens to hundreds of microseconds in these studies.

To induce cavitation bubbles a Q-switched Nd:YVO4 pulsed laser beam with a wavelength of 532 nm, a 15 nsec pulse width, and a maximum repetition frequency of 100 KHz was focused through a 100× objective lens into the PLDG device. Other wavelengths, such as UV, visible, and infrared may also be suitable. Droplet generation was captured using a time resolved imaging system. FIG. 8 shows a series of such images obtained during droplet generation. Using corn oil for a continuous oil phase and phosphate buffered saline (PBS) for an aqueous phase, corn oil and PBS flow rates were adjusted to form a stable interface at the nozzle opening (FIG. 8, panel (a)). Cavitation bubble formation is initiated within 1 microsecond of the initiating laser pulse (FIG. 8 panel (b)) and reaches maximum size within 3 microseconds, pushing PBS into the corn oil channel (FIG. 8, panel (c)). The bubble begins to collapse after 5 microseconds (FIG. 8, panel (d)). As the cavitation bubble collapses a narrow neck is formed between the PBS fluid channel and the extruded droplet (FIG. 8, panels (d) to (f)). This connection severs due to hydrodynamic instability (FIG. 8, panel (g)). As a result a 137 pL droplet was generated using a 100 microjoule laser pulse in about 500 microseconds, then transported away by flow through the corn oil channel (FIG. 8, panels (h) and (i)8H).

Example 2

Volume Control of Droplets Generated by PLDG

The volume of PLDG can be controlled can be controlled by adjusting the energy delivered by the pulse laser, which is a function of laser intensity and pulse duration, the location of the laser excitation, or a combination of the above. Alternatively, the energy of the pulse laser may be adjusted using a beam polarizer.

Figure 9:
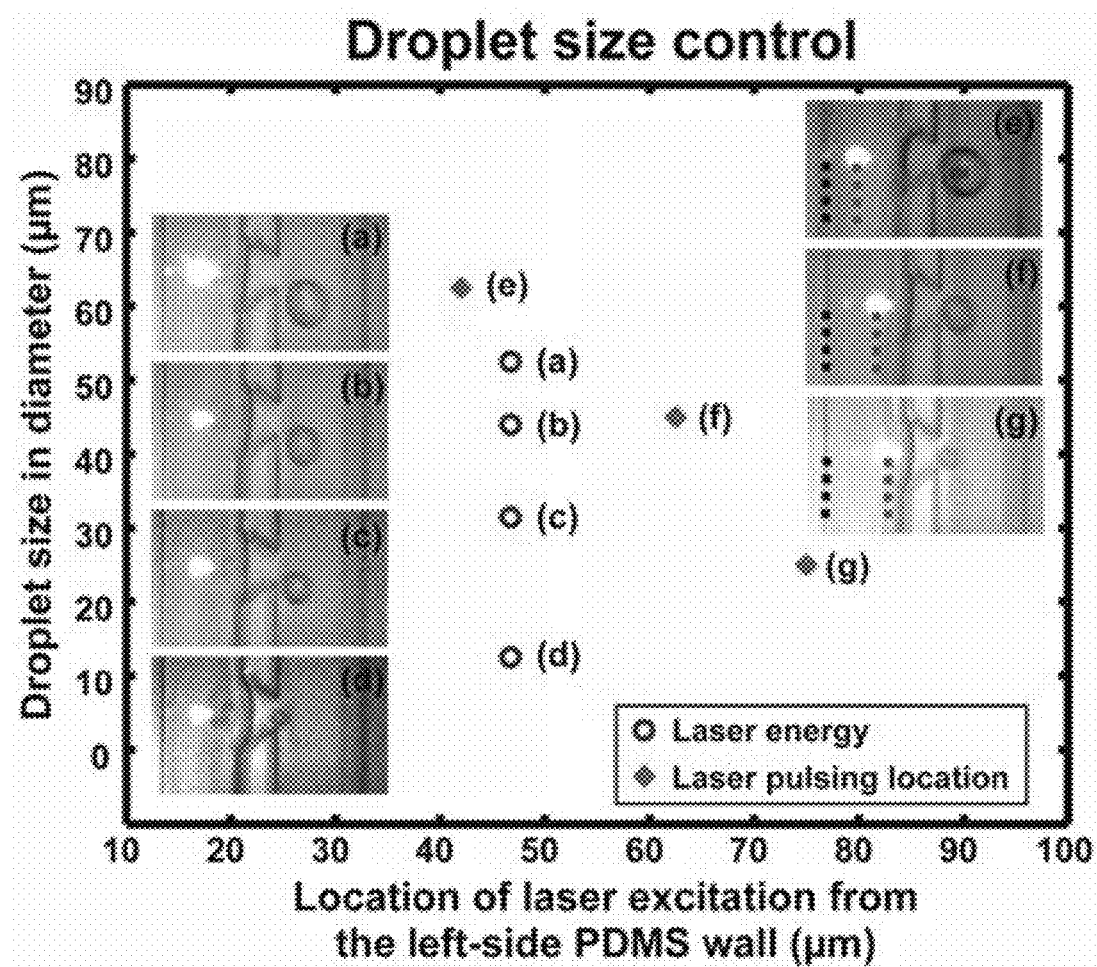
FIG. 9 depicts modulation of the volume of a generated droplet by varying the energy of the laser pulse and by varying the location of the laser pulse.

FIG. 9 illustrates control of the volume of droplets produced by PLDG by adjusting these parameters. Droplets indicated by FIG. 9, panes (a) to (d), show the effects of varying the laser energy (FIG. 9, panel (a)=100 microjoules, panel (b)=90 microjoules, panel (c)=80 microjoules, panel (d)=70 microjoules) at a fixed distance of 47 microns from the nozzles. This produces controlled droplet sizes ranging from about 55 to about 5 microns, decreasing with decreasing laser energy.

Control of droplet size is shown in FIG. 9 in panels (e) to (g), where laser energy is held constant at 100 microjoules and the distance of the focus point to the nozzle is adjusted between about 40 microns and about 80 microns. Droplet size decreases from about 60 microns to about 25 microns as the focus point is moved away from the corn oil/PBS interface. Using a combination of laser energy and focal point distance from the fluid interface droplet volume can be controlled between 1 pL to 150 pL.

Example 3

Consistency of the Size of Droplets Produced by PLDG

Figure 10:
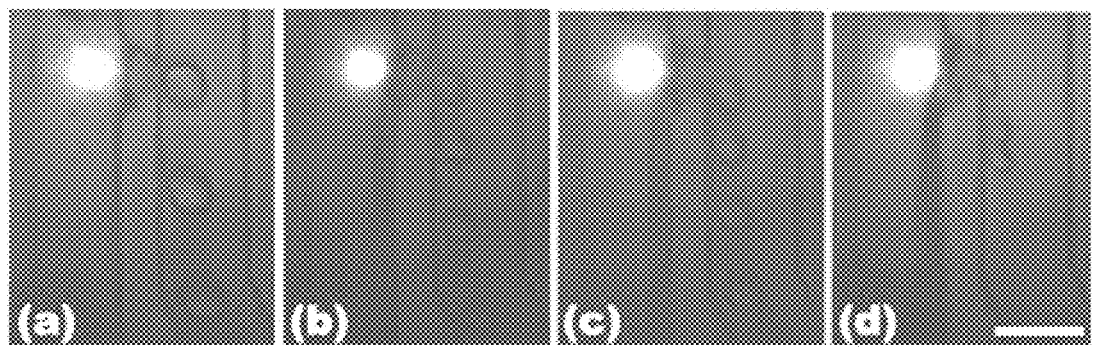
FIG. 10, panels (a)-(d), illustrate continuous generation of droplets within a fluid channel using a series of laser pulses repeated at different intervals. The scale bar has a length of 100 microns. Panel (a) illustrates 2 millisecond intervals, panel (b) illustrates 1 millisecond intervals, panel (c) illustrates 500 microsecond intervals, and panel (d) illustrates 100 microsecond intervals.

Since it is an on demand methodology, PLDG can produce droplets at different frequencies by controlling the interval between laser pulses. FIG. 10 shows the results of continuous droplet generation at different excitation intervals ranging from 2 msec (FIG. 10, panel (a)) to 100 microseconds (FIG. 10, panel (d)). The flow rate of the fluid channel receiving the droplets was adjusted to keep the droplets dispersed at high droplet generation rates.

Figure 11:
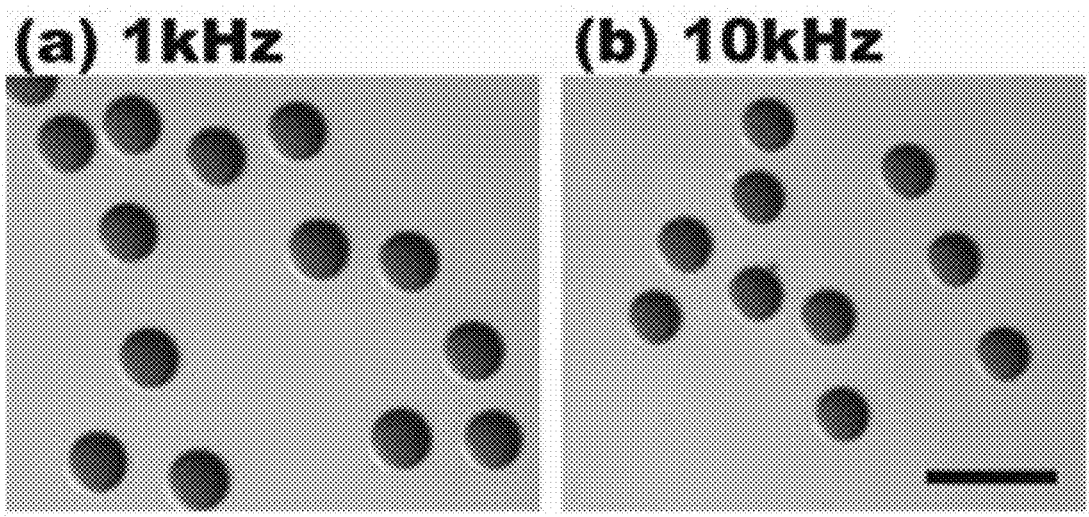
FIG. 11, panels a and b, illustrate collected droplets generated at different laser pulse frequencies. The scale bar has a length of 100 microns. Panel (a) illustrates droplets generated by a laser pulse frequency of 1 kHz. Panel (b) illustrates droplets generated by a laser pulse frequency of 10 kHz.
Figure 12:
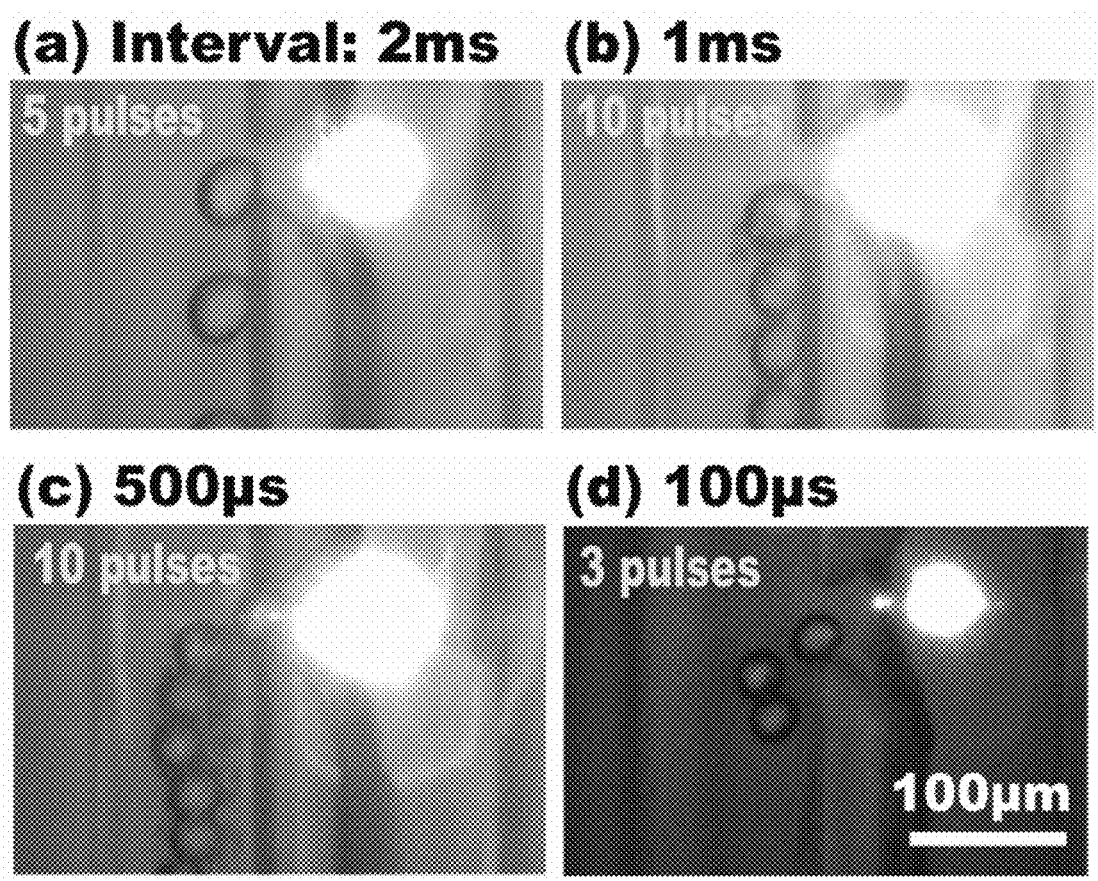
FIG. 12, panels a-d, illustrates continuous generation of droplets within a fluid channel using a series of laser pulses repeated at different intervals. Panel (a) illustrates 2 millisecond intervals, panel (b) illustrates 1 millisecond intervals, panel (c) illustrates 500 microsecond intervals, and panel (d) illustrates 100 microsecond intervals.

FIG. 11 shows illustrative e droplets collected at droplet generation frequencies of 1 kHz (panel (a)) and 10 kHz (panel (b)). Droplet size was consistent despite a 10 fold difference in the rate at which the droplets are formed. FIG. 12 shows results from a similar study, in which the interval between laser excitations was set at 2 msec (panel (a)), 500 microseconds (panel (b)), and 100 microseconds (panel (c)). Data collected from droplets generated at 500 microsecond intervals (2 kHz) showed a volume variation of 0.689%.

Figure 14:
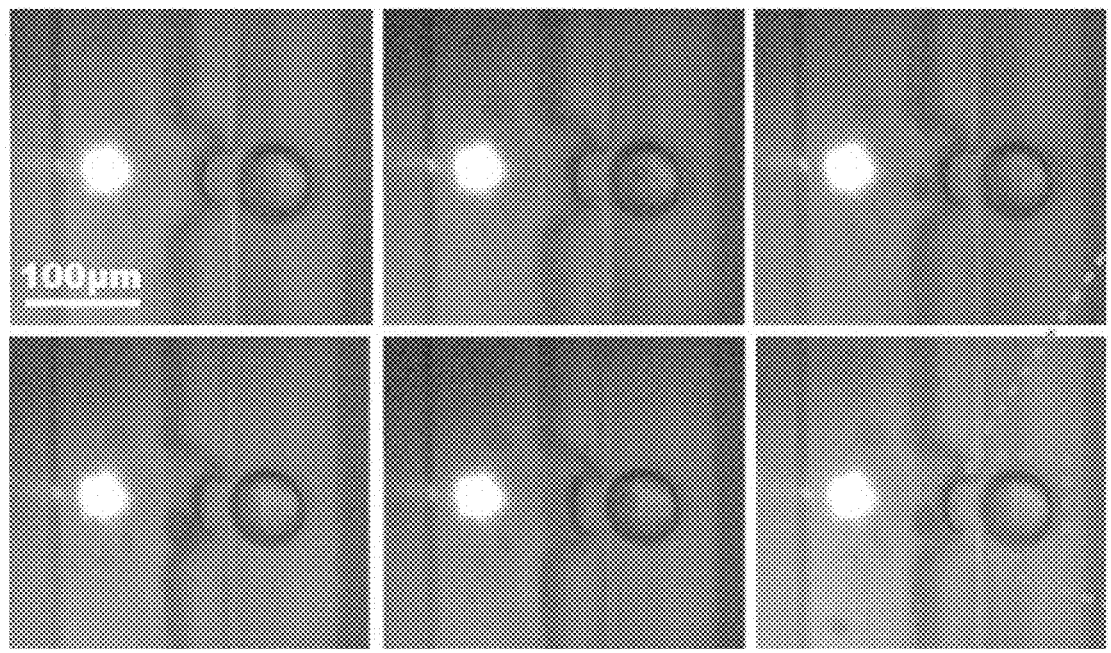
FIG. 14 illustrates consecutive generation of droplets within a fluid channel using laser pulses at a frequency of 1 Hz.

Continuous generation of droplets at different laser excitation intervals is shown in FIG. 14, with excitation intervals at 2 msec (panel (a)), 500 microseconds (panel (b)), and 100 microseconds (panel (c)). Using a pulse interval of 100 microseconds and a laser power of 90 microjoules a consistent droplet production rate of 10 kHz can be achieved.

Example 4

Encapsulation in Droplets by PLDG

Since it is an on demand methodology that also permits droplet volume control, PLDG permits the encapsulation of specified contents of a fluid channel as droplets in a second fluid channel. An example of such an application is the encapsulation of a single particle or cell designated from a stream of particles or cells passing through a PLDG device, as directed by a controller based on data received from a monitor. Such a particle or cell could be isolated within a droplet of growth media and carried by a second fluid channel for further characterization.

Figure 13:
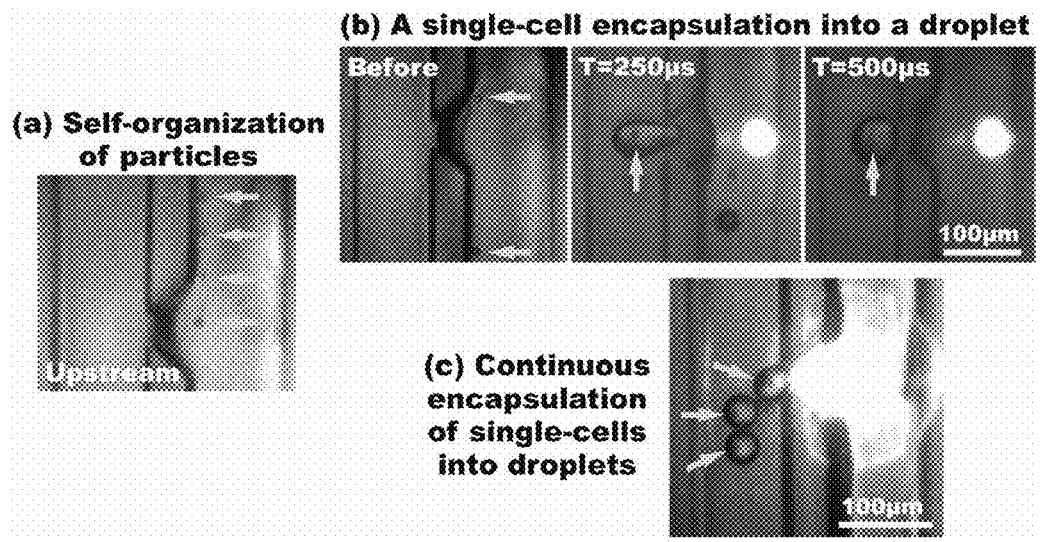
FIG. 13, panels a-c, depict encapsulation of a particle or cell within a droplet generated by a cavitation bubble. Panel (a) shows particles within a fluid channel. Panel (b) shows the position of a cell, indicated by a white arrow, before and at different time intervals following the induction of a cavitation bubble and subsequent generation of a droplet. Panel (c) illustrates continuous generation of series of droplets that each encapsulate a cell.

This is shown in FIG. 13. In FIG. 13, panel (a), particles (indicated by white arrows) are shown in s fluid channel of a PLDG device. Generation of the encapsulating droplet is shown in FIG. 13, panel (b). The droplet seen extruding through the nozzle at 250 microseconds from induction of the cavitation bubble can be seen to enclose a particle. FIG. 13, panel (c), shows results of a similar study, with continuous capture of cells. Encapsulation of live HeLa cells in this fashion shows high viability rates (92.07%). PLDG device reliability has been tested by continuously applying laser pulses at a rate of 10 kHz for one hour, corresponding to the generation of 3.6 million cavitation bubble generations with no observable damage to the device.

Droplet generation methods and devices that are particularly suited to use in microfluidic devices have been disclosed. These provide for rapid, on demand droplet generation at rates as high as 100 kHz. Droplet volume can be adjusted and has been shown to be highly reproducible, with volume differences of less than 1%. The disclosed devices do not utilize mechanical parts, and the use of an externally located directed energy source (for example a pulse laser) greatly simplifies design of both the device and supporting equipment. It should also be noted that the efficiency and inherent simplicity of the PLDG approach may have utility outside of the field of microfluidics. The high rate of droplet production and the narrow size distribution of the resulting droplets indicate that such methods and devices may have utility in the preparation of emulsions where consistency of the droplet size is paramount. Examples include but are not limited to pharmaceuticals, including vaccine compositions. The high rate of droplet production and the ability to control the volume of droplets as they are extruded indicate that such methods and devices may have utility in the deposition of generated droplets across a fluid/gas interface and onto solid surfaces, thereby depositing and localizing nonvolatile droplet contents. Examples of such uses include but are not limited to high resolution printing and generation of microarrays. It should be apparent, however, to those skilled in the art that many more modifications besides those already described are possible without departing from the inventive concepts herein It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes. However, where a definition or use of a term in a reference, which is incorporated by reference herein is inconsistent or contrary to the definition of that term provided herein, the definition of that term provided herein applies and the definition of that term in the reference does not apply. The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method for generating droplets in a device comprising:
  providing
    a first fluid stream comprising a first fluid flowing in a laminar flow;
    a second fluid stream comprising a second fluid flowing in a laminar flow adjacent to said first fluid stream where said second fluid is a different fluid than said first fluid; and
  using a laser to generate a cavitation bubble in the first fluid stream, wherein the cavitation bubble imparts sufficient velocity to a portion of the first fluid so as to extrude a droplet of the first fluid into the second fluid stream where said droplet is formed as a discrete droplet in said second fluid stream.

2. The method of claim 1, wherein:
  said first fluid stream is in a first microfluidic channel;
  said second fluid stream is in said second microfluidic channel; and
  an opening fluidly couples said first microfluidic channel to said second microfluidic channel; and
  said cavitation bubble imparts sufficient velocity to a portion of the first fluid so as to extrude a droplet of the first fluid across the opening and into the second microfluidic channel where said droplet is formed as a discrete droplet in said microfluidic channel.

3. The method of any one of claim 1 or 2, wherein the first fluid and the second fluid are respectively immiscible to each other.

4. The method of claim 1, wherein the cavitation bubble is generated by irradiation of a volume of the first fluid using a pulse laser.

5. The method of claim 4, further comprising selecting at least one of an intensity, duration, wavelength, and position of the irradiation produced by said pulse laser to thereby produce a desired volume of the droplet.

6. The method of claim 4, wherein the first fluid and the second fluid are respectively immiscible to each other.

7. The method of claim 6, wherein the first fluid comprises an aqueous fluid.

8. The method of claim 7, wherein the second fluid comprises an oil or an organic solvent.

9. The method of claim 4, wherein the irradiation is initiated by a controller controlling said pulse laser.

10. The method of claim 9, further comprising a step of selecting at least one of timing of occurrence of pulses emitted by the pulse laser, frequency of occurrence of pulses emitted by the pulse laser, wavelength of pulses emitted by the pulse laser, energy of pulses emitted by the pulse laser, and aiming or location of pulses emitted by the pulse laser.

11. The method of claim 9, further comprising monitoring via a monitor the second fluid path and transmitting data generated by such monitoring to said controller.

12. A device for generating droplets comprising:
  a first microfluidic channel containing a first fluid;
  a second microfluidic channel containing a second fluid that is different than said first fluid;
  an opening between the first microfluidic channel and the second microfluidic channel;
  a laser; and
  a controller coupled to said laser and configured to operate said laser to induce temporary formation of one or more cavitation bubbles in the first fluid in said first microfluidic channel to form a bubble in the first fluid effective to thereby extrude a droplet of the first fluid through the opening into the second microfluidic channel where said droplet is formed as a discrete droplet in said second fluid.

13. The device of claim 12, wherein the controller is configured to adjust volume of the droplet as a function of at least one of timing of occurrence of pulses emitted by the laser, frequency of occurrence of pulses emitted by the laser, wavelength of pulses emitted by the laser, energy of pulses emitted by the laser, and aiming or location of pulses emitted by the laser.

14. The method of claim 12, wherein the first fluid and the second fluid are respectively immiscible to each other.

15. The device of claim 12, wherein said laser is a pulse laser configured to produce a substantially continuous volume tuning of droplet size ranging from about 0.1 fL to about 1µL.

16. The device of claim 12, wherein said laser is a pulse laser configured to provide on-demand droplet generation at a speed of greater than about 1,000 droplets/sec.

* * * * *